(12) United States Patent
Ure et al.

(10) Patent No.: US 8,288,162 B2
(45) Date of Patent: Oct. 16, 2012

(54) NANO-PARTICLE BIOCHIP SUBSTRATES

(75) Inventors: David A. Ure, Somerville, MA (US);
Richard E. Palmer, Hagley (GB)

(73) Assignee: Inanovate, Inc., Somerville, MA (US)

( * ) Notice: Subject to any disclaimer, the term of this patent is extended or adjusted under 35 U.S.C. 154(b) by 0 days.

(21) Appl. No.: 11/729,510

(22) Filed: Mar. 28, 2007

(65) Prior Publication Data
US 2008/0038830 A1 Feb. 14, 2008

Related U.S. Application Data

(60) Provisional application No. 60/786,805, filed on Mar. 28, 2006.

(51) Int. Cl.
*B32B 5/16* (2006.01)
*G01N 33/00* (2006.01)
(52) U.S. Cl. ............. 436/73; 436/86; 977/773; 428/323
(58) Field of Classification Search ............ 436/86, 436/73; 977/773; 428/323
See application file for complete search history.

(56) References Cited

U.S. PATENT DOCUMENTS

| | | | |
|---|---|---|---|
| 6,406,921 B1 | 6/2002 | Wagner et al. | |
| 6,582,969 B1 | 6/2003 | Wagner et al. | |
| 6,720,157 B2 | 4/2004 | Indermuhle et al. | |
| 6,730,537 B2 | 5/2004 | Hutchison et al. | |
| 7,274,458 B2 * | 9/2007 | Perez et al. | 356/445 |
| 2002/0098526 A1 * | 7/2002 | Bamdad | 435/7.9 |
| 2005/0827560 | 12/2005 | Viswanadham et al. | |

FOREIGN PATENT DOCUMENTS

| | | |
|---|---|---|
| EP | 1 579 912 | 9/2005 |
| WO | WO 01/60316 | 8/2001 |

OTHER PUBLICATIONS

Taleb, A., Petit, C., Pileni, & M.P. (1997). Synthesis of Highly Monodisperse Silver Nanoparticles from AOT Reverse Micelles: A Way to 2D and 3D Self-Organization. Chemistry of Materials, 9, 950-959.*
Chuang et al., Monitoring Self-assembly Processes by Characterizing Optical Properties of Gold Nanoparticles: Microprocesses and Nanotechnology Conference (2005) Tokoyo Japan.
Collins et al., "Clusters for biology: Immobilisation of proteins by size-selected metal clusters" Applied Surface Science (2004) 226(1-3): 197-208.
Couillard et al, "Metastable ordered arrays of size-selected Ag cluster on graphite".
Fort et al., "Metallic nano-structured substrates for enhanced fluorescence bio-analysis".
Leung et al., "Immobilization of protein molecules by size-selected metal clusters on surfaces" Adv Materials (2004) 16(3); 223-226.

(Continued)

*Primary Examiner* — Krishnan S Menon
*Assistant Examiner* — Rebecca M Fritchman
(74) *Attorney, Agent, or Firm* — Wolf, Greenfield & Sacks, P.C.

(57) ABSTRACT

The present invention relates to a nano-particle biochip substrate comprising a substrate having attached thereto (bearing), on or in a surface, nano-particles having a cross sectional diameter of from about 0.1 nm. to about 50 nm. and useful to immobilize one or more moieties of interest.

40 Claims, 9 Drawing Sheets

OTHER PUBLICATIONS

McMillan et al., "Ordered nanoparticle arrays formed on engineered chaperonin protein templates" Nature Materials (2002) 1: 247-252.
Palmer et al., "Nanostructured surfaces from size-selected clusters" Nature Materials (2003) 2: 443-448.
Pratontep et al., "Scaling Relations for Implantation of Size-Selected Au, Ag, and Si Clusters into Graphite" Phys Rev Lett. (2003) Feb. 7;90(5):055503.
Prisco et al., "Residue-specific immobilisation of protein molecules by size-selected clusters" J of Royal Society (2005) 2(3): 169-175.
Xirouchaki et al. "Deposition of size-selected metal clusters generated by magnetron sputtering and gas condensation" Philos Transact A Math Phys Eng Sci. (2004) Jan. 15;362(1814):117-24.
Yan et al. "Metallic nanostructures for plasmonic sensors using surface-enhanced fluorescence and Raman detection".

* cited by examiner

NANO-PARTICLE BIOCHIP SUBSTRATES

CROSS-REFERENCE TO RELATED APPLICATION

This application claims the benefit of the filing date of U.S. Provisional Application No. 60/786,805 filed Mar. 28, 2006, entitled "CHIPS USING EMBEDDED NON-BIOLOGICAL CLUSTERS TO IMMOBILIZE BIOLOGICAL MATERIAL". The referenced application is hereby incorporated by reference in its entirety for all purposes.

FIELD OF THE INVENTION

The invention relates primarily to the field of nanotechnology. More specifically, the invention pertains to nano-particles and nano-particle structures patterned onto a surface, as well as the use of such nano-particle patterned surfaces in various bio-chip applications.

BACKGROUND OF THE INVENTION

Numerous scientific and commercial processes involve the interaction of one or more moiety (e.g. bio-molecules, catalyst etc.), either on, or in the presence of a surface. Biochips are available for use in assessing a wide variety of such interactions. However, in almost all instances, the efficiency or use of biochips is limited, at least in part, by the physical and chemical properties of the surface to which the moieties (bio-molecules and other specific molecules of interest) are attached, as well as the effects on the moieties that result from their interaction with the surface. It would be useful to have additional types of biochips available, particularly biochips that do not have the performance limitations of biochips now being used.

SUMMARY OF THE INVENTION

A novel 'nano-particle biochip substrate' is disclosed. The 'nano-particle biochip substrate' includes a base of at least one surface, with the topmost surface patterned with at least one nano-particle and typically a plurality of nano-particles (also referred to herein as clusters). The nano-particles are attached (pinned, embedded, grown on, or otherwise affixed) on or in the substrate surface, such that they are stable on the surface under conditions under which the nano-particle biochip substrate and nano-particle biochips are used. Methods of using attached nano-particles on a surface, such as for immobilizing moieties, such as bio-molecules (e.g. proteins, peptides, antibodies, antibody fragments and a wide variety of additional types of bio-molecules) and catalysts, along with associated bio-chip applications are also disclosed.

In one embodiment, the invention is a nano-particle biochip substrate comprising a substrate having attached thereto (bearing), on or in a surface, nano-particles having a cross sectional diameter (in which a cross sectional diameter is) from about 0.1 nm. to about 50 nm. and useful to immobilize one or more (at least one, a) moieties of interest. In specific embodiments, the nano-particles useful to immobilize one or more moieties of interest have a cross sectional diameter of from about 1 nm. to about 10 nm. In further embodiments, the nano-particles useful to immobilize one or more moieties of interest have a cross sectional diameter of from about 3 nm. to about 7 nm. Nano-particles can be attached on (to) a surface of the substrate or in a surface of the substrate (positioned within or partially within a surface of the substrate).

The present invention relates to a nano-particle biochip substrate comprising a substrate having attached thereto (bearing), on or in a surface, nano-particles having a cross sectional diameter of from about 0.1 nm. to about 50 nm. and useful to immobilize one or more moieties of interest. In specific embodiments of the invention, the nano-particles have a cross sectional diameter of from about 1 nm. to about 10 nm. or a cross sectional diameter of from about 3 nm. to about 7 nm. In further embodiments of the nano-particle biochip substrate of this invention, the nano-particles attached to the surface have a cross sectional diameter of greater than 50 nm and a functional or exposed diameter that is less than 50 mm.

The nano-particle biochip substrate can comprise a substrate having attached thereto (bearing), either on or in a surface, nano-particles that are controlled for size. For example, the nano-particle biochip substrate comprises a substrate having attached thereto, either on or in a surface, nano-particles controlled for size, such that the average variation in cross sectional diameter of the nano-particles on the surface is less than 1%; less than 2%; less than 5%; less than 10%; less than 25%; less than 50%; less than 100%; or less than 200%. The average variation in cross sectional diameter of the nano-particles on the surface can be less than 200%, such as any specific value less than 200% (e.g., one value, such as 1, 2, 5, 10, 25, 50, 100, less than 200%). In specific embodiments, the average cross sectional diameter of the nano-particles is controlled for size, such that the average variation in cross sectional diameters of the nano-particles on the surface is a value less than from about 1% to about 50% (any value between less than 1% up to and including 50%).

In certain embodiments, the nano-particle biochip substrate can comprise a substrate having attached thereto (bearing), either on or in a surface, nano-particles, wherein the nano-particles are attached such that the average distance between the nano-particles and their respective nearest neighbors on the surface is a value from about 1 mm to about 200 nm. For example, the distance can be any value between 1 nm. and 200 nm., such as 1, 5, 10, 15, 20 or any other value between 1 nm. and 200 nm. The nano-particle biochip substrate of the present invention can be configured such that the average distance between nano-particles and their respective nearest neighbors on the substrate surface in a first area of the surface differs from the average distance between nano-particles and their respective nearest neighbors in a second area of the surface by less than 1%; less than 2%; less than 5%; less than 10%; less than 25%; less than 50%; less than 100%; or less than 200%, wherein the first area and the second area are each equal to or greater than 4000 $nm^2$ in size. Alternatively, in some embodiments, the average distance between nano-particles and their respective nearest neighbors on the surface in a first area of the nano-particle biochip substrate surface differs from the average distance between nano-particles and their respective nearest neighbors in a second area of the surface by less than 1%; less than 2%; less than 5%; less than 10%; less than 25%; less than 50%; less than 100%; or less than 200%, wherein the first area and the second area are each equal to or greater than 100 $nm^2$ in size. In a further embodiment of the nano-particle biochip substrate, the average distance between nano-particles and their respective nearest neighbors on the surface in a first area of the surface differs from the average distance between nano-particles and their respective nearest neighbors in a second area of the surface by less than 1%; less than 2%; less than 5%; less than 10%; less than 25%; less than 50%; less than 100%; or less than 200%, wherein the first area and the second area are each equal to or greater than 1 $micron^2$ in size.

In further embodiments, the nano-particle biochip substrate has attached thereto, either on or in a surface thereof, such nano-particles and the average distance between nano-particles and their respective nearest neighbors on the surface varies randomly. The nano-particle biochip substrate can comprise, in further embodiments, a substrate having attached thereto, either on or in a surface, such nano-particles, wherein the average distance between nano-particles and their respective nearest neighbors on the surface varies in a pre-selected pattern across the surface.

In all embodiments of the invention, in which the nano-particle biochip substrate comprises a substrate having attached thereto (bearing), on or in a surface, nano-particles having a cross sectional diameter of from about 0.1 nm. to about 50 nm., from about 1 nm. to about 10 nm. or from about 3 nm. to about 7 nm and useful to immobilize one or more moieties of interest, the number of nano-particles in a first area of the surface can differ from the number of nano-particles in a second area of the surface by less than 1%; less than 2%; less than 5%; less than 10%; less than 25%; less than 50%; less than 100%; or less than 200%, wherein the first area and the second area are each equal to or greater than 4000 $nm^2$ in size. Alternatively, the first area and the second area are each equal to or greater than 100 $nm^2$ in size or equal to or greater than 1 $micron^2$ in size. In certain embodiments, the number of nano-particles in a first unit area on the surface varies randomly to the number of nano-particles in a second unit area on the surface and in other embodiments, the number of nano-particles in a unit area on the surface varies in a pre-selected pattern (such as a gradient) to the number of nano-particles in one or more other unit areas on the surface. In either embodiment, each unit area can be equal to or greater than 100 $nm^2$ in size; equal to or greater than 4000 $nm^2$ in size; or equal to or greater than 1 $micron^2$ in size.

In another embodiment, the invention is a nano-particle biochip substrate comprising a substrate having attached thereto (bearing), on or in a surface, nano-particles having a cross-sectional diameter of from about 0.1 nm. to about 50 nm. and useful to immobilize one or more moieties of interest, wherein the nano-particles have attached thereto at least one linker capable of immobilizing a moiety or moieties of interest. In specific embodiments, the nano-particles have a cross-sectional diameter of from about 1 nm. to about 10 nm. or a cross-sectional diameter of from about 3 nm. to about 7 nm. In further embodiments, the nano-particles have a cross sectional diameter of greater than 50 nm and the functional or exposed diameter is less than 50 nm. In these embodiments or other alternative configurations, each linker attached to a nano-particle has a specific affinity for at least one specific moiety or at least one specific area or bond on at least one moiety of interest. Linkers can comprise a wide variety of materials, such as a small molecule, wherein a small molecule is (a) a small molecule with at least one carboxyl group or at least one amine group on one functional end; (b) a small molecule with at least one sulfur group on at least one functional end; (c) a small molecule with at least one carboxyl group or at least one amine group on one functional end and at least one sulfur group on at least one functional end; (d) a small molecule with one functional end that interacts with an amino acid and one functional end that interacts with a nano-particle; (e) a small molecule with one functional end that interacts with an amino acid and one functional end that interacts with a nano-particle; (f) a small molecule with one functional end that interacts with a strand or sequence of DNA and one functional end that interacts with a nano-particle; (g) a small molecule with one functional end that interacts with a gene or gene sequence and one functional end that interacts with a nano-particle; (h) a small molecule with one functional end that interacts with a lipid and one functional end that interacts with a nano-particle; (i) a small molecule with one functional end that interacts with a sugar and one functional end that interacts with a nano-particle; (j) a small molecule with one functional end that interacts with an salt and one functional end that interacts with a nano-particle; (k) a small molecule with one functional end that interacts with a cell lysate and one functional end that interacts with a nano-particle; (l) a small molecule with one functional end that interacts with a protein and one functional end that interacts with a nano-particle; (m) a small molecule with one functional end that interacts with an antibody or antibody fragment and one functional end that interacts with a nano-particle; (n) a small molecule with one functional end that interacts with an aptamer and one functional end that interacts with a nano-particle; (o) a small molecule with one functional end that interacts with a cell and one functional end that interacts with a nano-particle; or (p) a small molecule with one functional end that interacts with a peptide and one functional end that interacts with a nano-particle. Any combination of such small molecules can be used. Many small molecules are useful as linkers, such as, but not limited to, a small molecule that has a formula selected from the group consisting of: (a) HS—R—COOH, HS—R—$NH_2$, (HS—$R_1$)$_n$—$R_2$—COOH, (HS—$R_1$)$_n$—$R_2$—$NH_2$; wherein the R, R1, and R2 can be any alkane, arene, or other suitable chemical group; (b) 4-mercaptobenzoic acid (HS—$C_6H_4$—COOH), (c) cysteamine (HS—$CH_2$—$CH_2$—$NH_2$), (d) (HS—$(CH_2)_3)_2$—$C_6H_4$—COOH, (e) (HS—$(CH_2)_4$—$O)_2$—$C_6H_4$—$(OCH_2)_{10}$—COOH, and (f) (HS—$(CH_2)_4$—$O)_2$—$C_6H_4$—$(OCH_2)_{20}$—$NH_2$].

Another embodiment of this invention is a nano-particle biochip substrate comprising substrate having attached thereto (bearing), on or in a surface, nano-particles having a cross-sectional diameter of from about 0.1 nm to about 50 nm and useful to immobilize one or more moieties of interest, wherein the nano-particles comprise a material that has an affinity for a moiety of interest or a linker molecule. The nano-particles can have a cross-sectional diameter of from about 1 nm. to about 10 nm. or a cross-sectional diameter of from about 3 nm. to about 7 nm. In a further embodiment, the nano-particles have a cross sectional diameter of greater than 50 nm and the functional or exposed diameter is less than 50 nm. In one embodiment described herein, nano-particles can be selected in order to permit only one moiety of interest to attach to each nano-particle on the substrate. In further embodiments, nano-particles can be selected to permit more than one moiety of interest (e.g., 2, 3, 4, etc.) to attach to each nano-particle on the substrate.

A wide variety of materials that have an affinity for a moiety of interest or a linker molecule are suitable for use in the present invention. They include, but are not limited to, gold; silver; platinum; copper; phosphorus; nickel; aluminum; cesium; palladium; carbon; magnesium; silicon; titanium; chromium; manganese; iron; cobalt; zinc; gallium; germanium; selenium; krypton; rubidium; strontium; zirconium; cadmium; tin; xenon; barium; tantalum; tungsten; iridium; thallium; lead; bismuth; polonium; radium; thorium; uranium; plutonium; americium; californium; einsteinium; fermium; nobelium; rutherfordium; bohrium; teflon; an oxide, an inorganic compound, or a mixture, an alloy or a combination of any of the foregoing.

A further embodiment of the invention is a nano-particle biochip substrate comprising a substrate having attached thereto (bearing), on or in a surface, nano-particles having a cross-sectional diameter of from about 0.1 nm to about 50 nm and useful to immobilize one or more moieties of interest, wherein the nano-particles (a) protrude above the surface surrounding the nano-particle; (b) are in cavities in the surface; (c) are positioned at the same level as the surrounding surface; or (d) a combination of (a), (b) and/or (c). In specific embodiments, the nano-particles have a cross-sectional diameter of from about 1 nm to about 10 nm or from about 3 nm. to about 7 nm. Alternatively, the nano-particles have a cross sectional diameter of greater than 50 nm. and the functional or exposed diameter is less than 50 nm. In certain embodiments, the nano-particles protrude above the nano-particle biochip substrate surface surrounding the nano-particles and the average height to which nano-particles protrude above the surface in a first area of the surface differs from the average height to which nano-particles protrude above the surface in a second area of the surface by less than 1%; less than 2%; less than 5%; less than 10%; less than 25%; less than 50%; less than 100%; or less than 200%. In other embodiments, the nano-particles are in cavities in the surface and the average depth of the cavities in a first area of the surface differs from the average depth of cavities in a second area of the surface by less than 1%; less than 2%; less than 5%; less than 10%; less than 25%; less than 50%; less than 100%; or less than 200%.

Also the subject of this invention is a nano-particle biochip substrate comprising a substrate having attached thereto (bearing), on or in a surface, nano-particles having a cross-sectional diameter of from about 0.1 nm to about 50 nm and useful to immobilize one or more moieties of interest, wherein the nano-particles (a) protrude above the surface surrounding the nano-particle; (b) are in cavities in the surface; (c) are positioned at the same level as the surrounding surface; or (d) a combination of (a), (b) and/or (c). Alternatively, the nano-particles have a cross-sectional diameter of from about 1 nm. to about 10 nm. or from about 3 nm. to about 7 nm. In a further embodiment, the nano-particles have a cross sectional diameter of greater than 50 nm. and the functional or exposed diameter is less than 50 nm. In the embodiments in which the nano-particles protrude above the surface surrounding the nano-particles, the average height to which nano-particles protrude above (extend beyond) the surface can vary or differ from one area/region or unit area on the substrate to another area or unit area/region on the substrate (different areas of the substrate can have nano-particles protruding from the surface at different average heights). In certain embodiments, the average height to which nano-particles protrude above (from) the surface of the nano-particle biochip substrate in a first area differs from the average height to which nano-particles protrude in a second area of the surface by less than 1%; less than 2%; less than 5%; less than 10%; less than 25%; less than 50%; less than 100%; or less than 200%. In the embodiments in which nano-particles are in cavities in the surface of the nano-particle biochip substrate, the average depth of the cavities can vary or differ from one area/region or unit area to another area/region or unit area on the substrate (different areas of the substrate can have nano-particles in cavities of different depths. In certain embodiments, the average depth of the cavities in a first area of the surface differs from the average depth of cavities in a second area of the surface by less than 1%; less than 2%; less than 5%; less than 10%; less than 25%; less than 50%; less than 100%; or less than 200%. In another embodiment of the invention, the nano-particle biochip substrate can comprise one or more areas in which nano-particles protrude above the substrate surface and one or more areas in which nano-particles are in cavities.

In a further embodiment of the invention, the nano-particle biochip substrate comprises a substrate having attached thereto, on or in a surface, nano-particles having a cross sectional diameter of from about 0.1 nm. to about 50 nm. and useful to immobilize one or more moieties of interest, wherein the nano-particles are distributed over a defined area in a controlled manner. Alternatively in these embodiments, the nano-particles have a cross-sectional diameter of from about 1 nm. to about 10 nm. or a cross-sectional diameter of from about 3 nm. to about 7 nm. In certain embodiments, the nano-particle biochip substrate of this invention has attached thereto (bears) nano-particles having a cross sectional diameter of greater than 50 nm. and a functional or exposed diameter of less than 50 nm. In some embodiments, the distribution of nano-particles over a defined area of the substrate surface is about (substantially) constant, such that the nano-particles are distributed in a regular pattern over the defined area. In one embodiment, the distribution results in a gradient of nano-particles on the surface. Alternatively, the distribution of nano-particles over a defined area is not constant, such that the average distance between nano-particles and their respective nearest neighbors is randomly distributed. In any of these embodiments in which the variation in density is controlled, it does not vary over a specified region by more than about 1%; about 2%; about 5%; about 10%; about 25%; about 50%; about 100%; or about 200%.

In any of the embodiments of the nano-particle biochip substrate, the surface of the biochip substrate can be comprised of a wide variety or materials and mixtures of materials. For example, the surface can comprise glass; chemically treated glass; silicon; mica; graphine; graphite; aldehyde; epoxy; strepavidin; biotin; silane; agarose; dextran; diamond; magnetic tape; at least one polymer, such as polyethylene glycol (PEG) or oligoethylene glycol (OEG); a carbon nano tube; gold; silver; copper; phosphorous; nickel; carbon; magnesium; titanium; iron; zinc; selenium; cadmium; tin; tungsten; lead; teflon; nitrocellulose; lipids; a hydrogel; a plastic; or rubber.

The surface of the nano-particle biochip substrate can be a single layer or may comprise two or more layers. In one embodiment, the nano-particle biochip substrate comprises one or more layers, wherein the one or more layers can independently be the same or different material. In a further embodiment, in which the surface of the substrate comprises at least two layers, each of the at least two layers can be composed of the same material or of different materials (e.g., each layer is composed of different material from the material from which a layer to which it is adjacent is composed). In a specific embodiment in which the surface of the substrate comprises at least three layers, each layer can be composed of the same material or of different materials (e.g., each layer may be composed of material different from the material from which an adjacent layer is composed).

The material of which the surface of the nano-particle biochip substrate is composed has an affinity for the one or more moieties of interest that is typically less than the affinity for the one or more moieties of interest of the nano-particles or linker molecules attached thereto. This facilitates attachment to nano-particles.

The surface of the nano-particle biochip substrate can be any of a variety of shapes and configurations. It will often be a flat surface or a curved surface. The substrate can be a slide, a micro-channel based device, a bead, a mass spectrometry device, a micro titer plate, a well-based device, a micro array slide, a bead based device, a disk, a membrane, a magnetic tape, an electronic tape, an optical tape, a lab on a chip based device, or a micro chip. In any of these embodiments, the surface can comprise two or more regions, wherein the average variation in cross sectional diameter of the nano-particles on the surface is from about 1% to about 50% and the average cross sectional diameter of the nano-particles in any one region is different from the average cross sectional diameter of the nano-particles in a different region on the surface. The average cross sectional diameter of the nano-particles can be controlled for size within one or more regions. Alternatively, the average cross sectional diameter of the nano-particles is not controlled for size within one or more regions. Further, in any of these embodiments, the surface can comprise two or more regions, wherein the average distance between nano-particles and their respective nearest neighbors on the surface in any one region is a value from about 1 nm to 200 nm, and the average variation in distance between nano-particles and their respective nearest neighbors in any other region on the surface is less than 1%; less than 2%; less than 5%; less than 10%; less than 25%; less than 50%; less than 100%; or less than 200%. Here, too, the surface can comprise two or more regions, wherein the average distance between nano-particles and their respective nearest neighbors on the surface in any one region is a specific value from about 1 nm to 200 nm, and is different from the average distance between nano-particles and their respective nearest neighbors on the surface in a different region. In certain embodiments, the number of nano-particles in any one region on the surface is different from the number of nano-particles in a different region on the same surface. In addition, in some embodiments in which the surface comprises two or more areas/regions or unit areas, the nano-particles in a region on the surface comprise materials different from materials of which nano-particles in a different region on the surface are comprised. Further, in some embodiments, the substrate surface comprises two or more regions and linker molecules are present on nano-particles. The linker molecules in a region on the surface can be different from the linker molecules present on nano-particles in a different region on the same surface. As described for other embodiments, the average protrusion of nano-particles above the surface in a region can be different from the average protrusion of nano-particles above the surface in a different region on the same surface. In specific embodiments of the nano-particle biochip substrate, wherein the surface comprises two or more regions, wherein (a) the average variation in cross sectional diameter of the nano-particles on the surface is from about 1% to about 50% and the average cross sectional diameter of the nano-particles in any one region is different from the average cross sectional diameter of the nano-particles in a different region on the surface; (b) the average number of nano-particles in any one region on the surface is different from the average number of nano-particles in a different region on the same surface; (c) the nano-particles in a region on the surface comprise materials different from materials of which nano-particles in a different region are comprised; (d) the linker molecules present on nano-particles in a region on the surface are different from the linker molecules present on nano-particles in a different region on the same surface; (e) the average protrusion of nano-particles above the surface in a region is different from the average protrusion of nano-particles above the surface in a different region on the same surface or (f) any combination of (a) through (e), such that a different moiety or moieties of interest are immobilized within each specified region. Here, too, the surface of the nano-particle biochip substrate can be a slide, a micro-channel based device, a bead, a mass spectrometry device, a micro titer plate, a well-based device, a micro array slide, a bead based device, a disk, a membrane, a magnetic tape, an electronic tape, an optical tape, a lab on a chip based device, or a micro chip.

A further embodiment of the nano-particle biochip substrate of the present invention comprises a substrate having attached thereto, on or in a surface, nano-particles having a cross sectional diameter of from about 0.1 nm. to about 50 nm. or from about 1 nm. to about 10 nm. or from about 3 nm. to about 7 nm and useful to immobilize one or more moieties of interest, wherein the nano-particles each additionally comprise one or more linker molecule and moieties of interest attach more favorably to linker molecules than to the surface of the nano-particle biochip substrate. In this embodiment, as well as the other embodiments described herein, nano-particles can be selected such that only one moiety of interest can attach to each nano-particle or such that more than one moiety of interest can attach to each nano-particle.

Also the subject of this invention is a nano-particle biochip, which comprises the nano-particle biochip substrate, in any of the embodiments described herein, and one or more moieties of interest, which can be attached to the nano-particles or to a linker attached to a nano-particle. The average cross sectional diameter of nano-particles used can be from about 0.1 nm to about 50 nm, from about 1 nm to about 10 nm. or from about 3 nm to about 7 nm. A biochip comprises (a) a substrate having attached thereto, on or in a surface, nano-particles having an average cross sectional diameter as specified herein and useful to immobilize one or more moieties of interest and (b) one or more moieties of interest attached to the nano-particles or to a linker attached thereto. The one or more moieties of interest can be a wide variety of materials, including but not limited to, proteins or peptides, antibodies or antibody fragments, amino acids; DNA; RNA; genes or portions thereof; lipids; sugars; salts; cell lysates; protein fragments; aptamers; or cells. Nano-particle biochips of this invention can be used for a variety of purposes and in a variety of formats, including many detection systems.

A further subject of this invention is methods of producing nano-particle biochip substrates and nano-particle biochips.

DESCRIPTION OF THE DRAWINGS

The following descriptions, each indicated by the number given, apply to the figures included in this document.

Label 1.—First surface of nano-particle biochip substrate: The first surface may be constructed from a wide range of materials as described herein. The nano-particles may optionally be deposited directly into/onto this surface. Alternatively, this surface may optionally be covered by a second surface, into/onto which nano-particles are deposited. The first surface may optionally take any planar, 2-dimensional, or three dimensional format;

Figure 1:
Figure 1:

Label 2.—Second surface (optionally covering first surface): The second surface may be constructed from a wide range of materials as described herein. The nano-particles may optionally be deposited directly into/onto this surface. Alternatively, this surface may optionally be covered by a third surface, into/onto which nano-particles are deposited. The second surface may optionally take any planar, 2-dimensional, or three dimensional format;

Label 3.—A nano-particle. Optionally composed of materials including, but not limited to, gold, silver, silicon, platinum, iron, copper, phosphorous, palladium, aluminum, cesium, nickel, tin, various oxides, etc. or alloys thereof. The nano-particles of this invention may range in size from an average cross sectional diameter of 0.1 nm up to 50 nm. The nano-particles may also be optionally be size specific, i.e. the average cross sectional diameter of each nano-particle within a chosen region on a base surface is substantially equivalent. Additional information in detailed description section;

Label 4.—Physical contact between the nano-particle and the first surface;

Label 5.—The average spacing between nano-particles on the base surface;

Label 6.—Represents the functional or exposed diameter of the nano-particles on the surface. This is defined as the diameter of the cross section of a nano-particle whereby the cross section is taken at, and parallel to, the boundary of (a) the layer onto or into which the nano-particle is attached, and (b) the surface environment.

Label 7.—Example of small molecule linker. In some embodiments, the linker molecules can include, but are not limited to, molecules that have one functional end that can be chemically or physically absorbed onto an amino acid or to any amino acid available bonds within a protein, and another functional end that can be chemically or physically absorbed direct onto the nano-particles;

Label 8.—Example of moiety. Illustrated here as an antibody, but can optionally be any type of bio-molecule or catalyst;

Label 9.—The average spacing between moieties. Optionally controlled to optimize the 'useful' moiety density in any unit area on a surface;

Label 10.—The analytes. In certain applications, such as bio-marker screening, bio-marker validation, or disease diagnosis, the analytes may be bio-markers for a certain disease. In other applications, such as general protein R&D and drug discovery and development, the analytes may be specifically targeted bio-molecules, and/or unknown bio-molecules (e.g. candidate bio-marker), and/or a drug compounds;

Label 11.—Primary 'labeled' antibodies. These primary 'probe' molecules allow the end user to gather information on the interactions occurring on the nano-particle biochip substrate;

Label 12.—The Labels. These may be any material that provides a signal to a user of the biochip, such as fluorescent, luminescent, or colorimetric tags;

Label 13.—Secondary 'labeled' antibodies. These secondary 'probe' molecules allow the end user to gather information on the interactions occurring on the nano-particle biochip substrate;

Label 14.—Incoming light from an SPR based reader device in transmission mode;

Label 15.—Incoming light from an SPR based or ellipsometry based reader device, in reflection mode;

Label 16.—In certain applications this will be a SPR based or ellipsometry based detector. In other applications, where alternative label free detection methods are used, e.g. recording a magnetic signal from the nano-particle biochip substrate, this could be a magnetic signal reading device;

Label 17.—The signal coming from the nano-particle biochip substrate carrying information relating to an interaction event;

Label 18.—An electronic based detection device set to record changes in one or more electronic properties across the nano-particle biochip system (e.g. resistance, current, voltage, capacitance, conductivity etc.);

Label 19.—Moieties (in this example antibodies, known as capture antibodies, which are laid down onto the biochip to interact with analytes);

Label 20.—'Function or active' sites of the moieties available for interaction (the area of the antibody that interacts with an analyte. Only highlighted in this example if the active site is available for interaction with an analyte, i.e. it is facing the right way, is functional, and is not hidden);

Label 21.—A 'standard' biochip surface, e.g. nitrocellulose membrane, hydrogel, treated glass, gold, silicon, or glass;

Label 22.—Nano-particles of the invention.

FIGS. 1(a) and (b): The base surface onto which the nano-particles of this invention are attached. FIG. 1(a) illustrates the base surface as only a first surface. FIG. 1(b) illustrates the base surface as a first surface and a second surface. The collective surfaces (the first surface (1), optionally covered by/coupled to a second surface (2), which in turn may be optionally covered by/coupled to a third surface, etc.), into/onto which topmost layer the nano-particles may be attached, are collectively referred to as the 'base' or 'background' surface.

Figure 2:
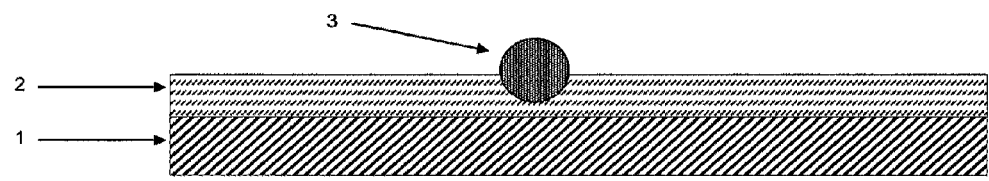
Figure 2:
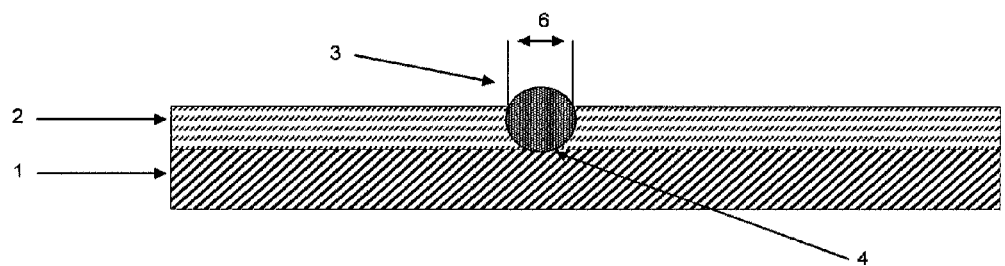

FIGS. 2(a) and (b): The base surface with a nano-particle attached to it. FIG. 2(a) illustrates the base surface with the nano-particle attached to the topmost surface, such that it is stable under normal biochip use conditions, and it is protruding from the topmost surface. FIG. 2(b) illustrates the base surface with a nano-particle attached to it, such that it is stable under normal biochip use conditions, and it is protruding from the topmost layer (the second surface), and it is also in contact with the first surface. Each represents an embodiment of the invention and can be classed as a nano-particle biochip substrate.

Figure 3:
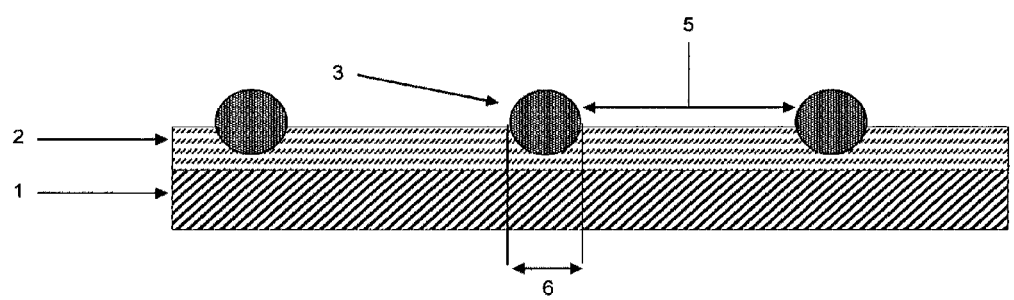

FIG. 3: Illustration of multiple nano-particles attached to a base surface, with the nano-particles at an optionally defined and controlled average spacing (the number and density of nano-particles in any unit area are optionally controlled). Represents an embodiment of the invention and can be classed as a nano-particle biochip substrate.

Figure 4:
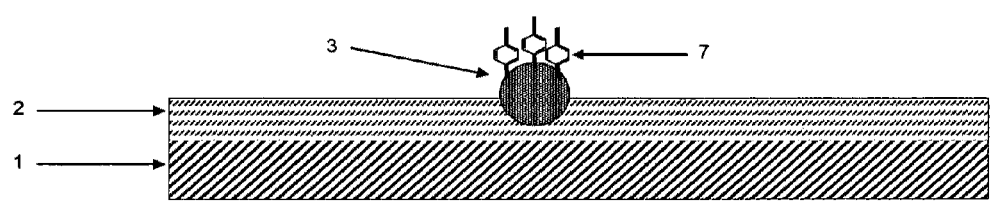
Figure 4:
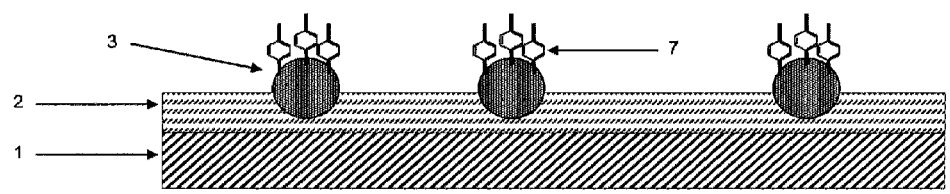

FIGS. 4(a) and (b): Illustrations of small molecule linkers attached to the nano-particles on the base surface. Each represents an embodiment of the invention and can be classed as a nano-particle biochip substrate. FIG. 4(a) illustrates just one nano-particle in a unit area on the base surface, with the nano-particle having small molecule linkers attached to it. FIG. 4(b) illustrates multiple size specific nano-particles in a unit are on the surface, each having small molecule linkers attached to them, and optionally being separated by a controlled average spacing (the number and density of the nano-particles in a unit area are optionally controlled).

Figure 5:
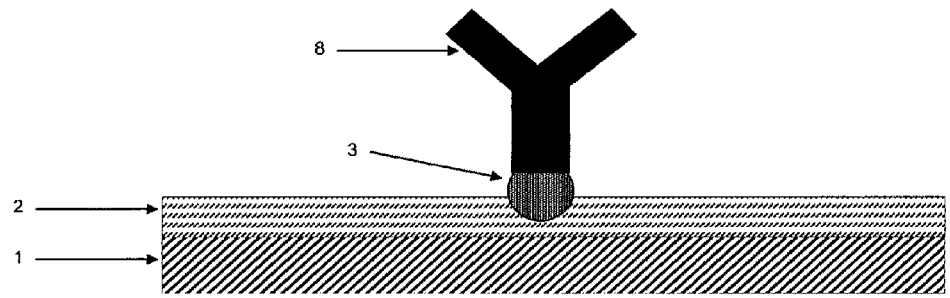
Figure 5:
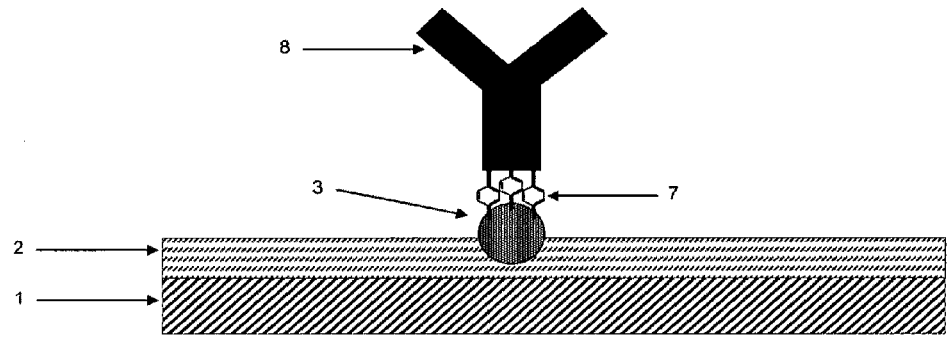

FIGS. 5(a) and (b): Illustration of a moiety (in these examples an antibody), attached to the nano-particle biochip substrate (one antibody attaches onto one nano-particle, either directly or via a small molecule linker). FIG. 5(a) illustrates direct attachment of the moiety to the nano-particle. FIG. 5(b) illustrates attachment of the moiety to the nano-particle via small molecule linkers. Each illustrates an embodiment of the invention.

Figure 6:
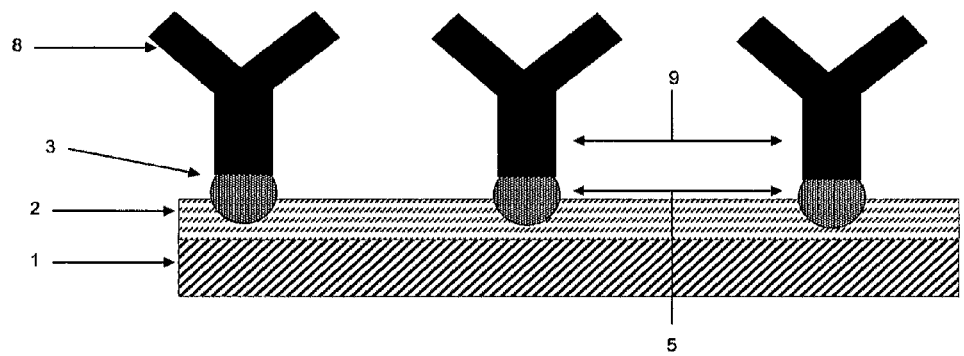
Figure 6:
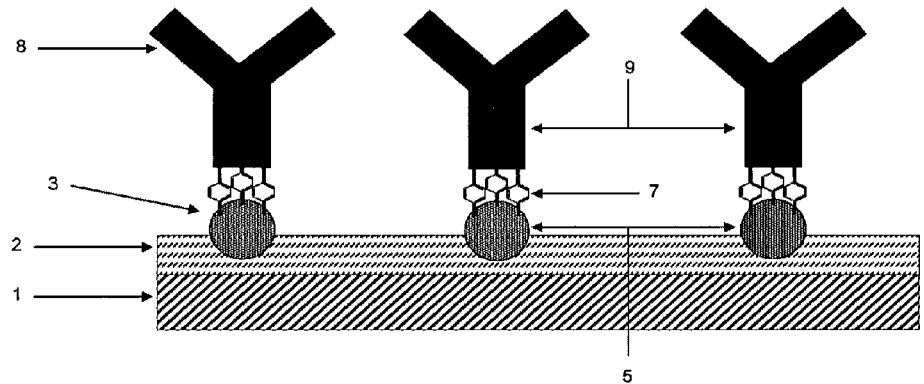

FIGS. 6(a) and (b): Illustration of multiple moieties (in these examples antibodies), attached to the nano-particle biochip substrate. With only one antibody attaching to each nano-particle on the surface, either directly or via a small molecule linker, and no antibodies attaching to the base surface itself FIG. 6(a) illustrates direct attachment of the moieties to the nano-particles. FIG. 6(b) illustrates attachment of the moieties to the nano-particle via small molecule linkers. Each illustrates an embodiment of the invention.

Figure 7:
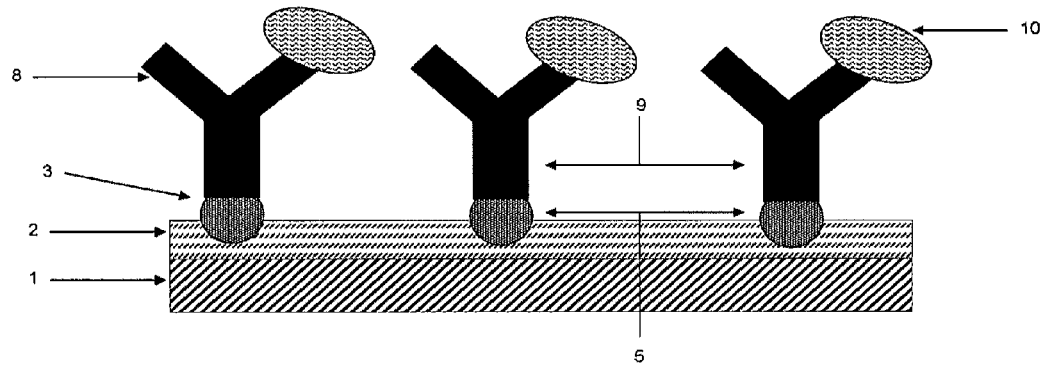
Figure 7:
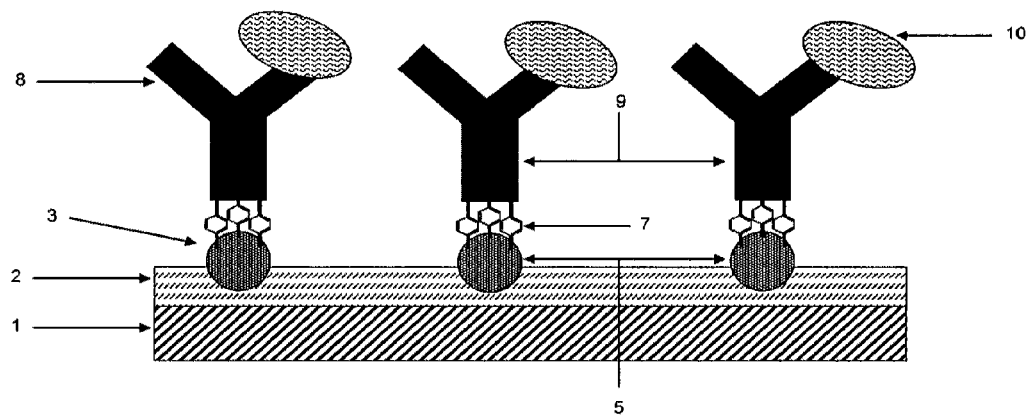

FIGS. 7(a) and (b): Illustration of multiple moieties (in these examples antibodies), attached to the nano-particle biochip substrate, which have interacted specifically with secondary bio-molecules (in this example antigens or analytes, specific to the antibody). FIG. 7(a) illustrates direct attachment of the moieties to the nano-particles. FIG. 7(b) illustrates attachment of the moieties to the nano-particle via small molecule linkers. Each illustrates how the nano-particle biochip substrate herein disclosed can optionally be used as a substrate for studying and interacting with bio-molecules.

Figure 8:
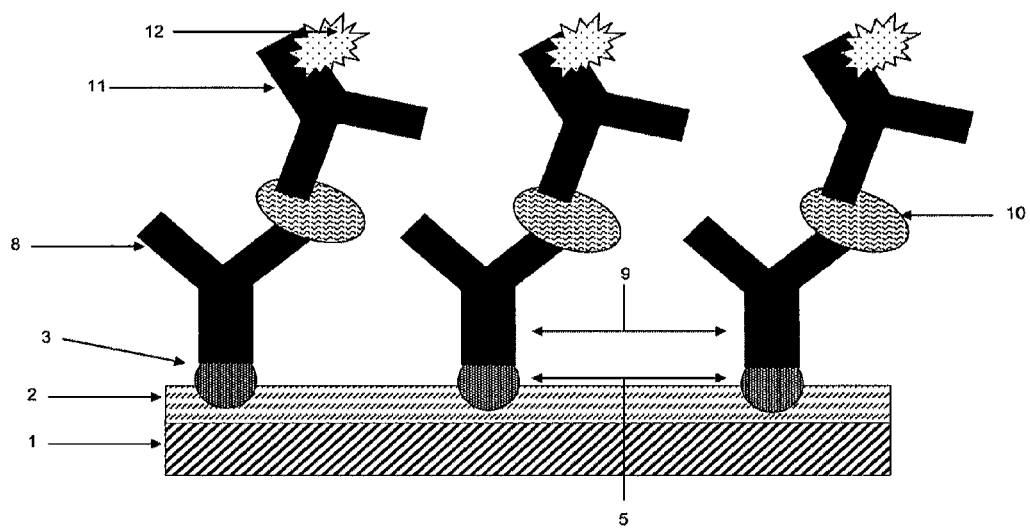
Figure 8:
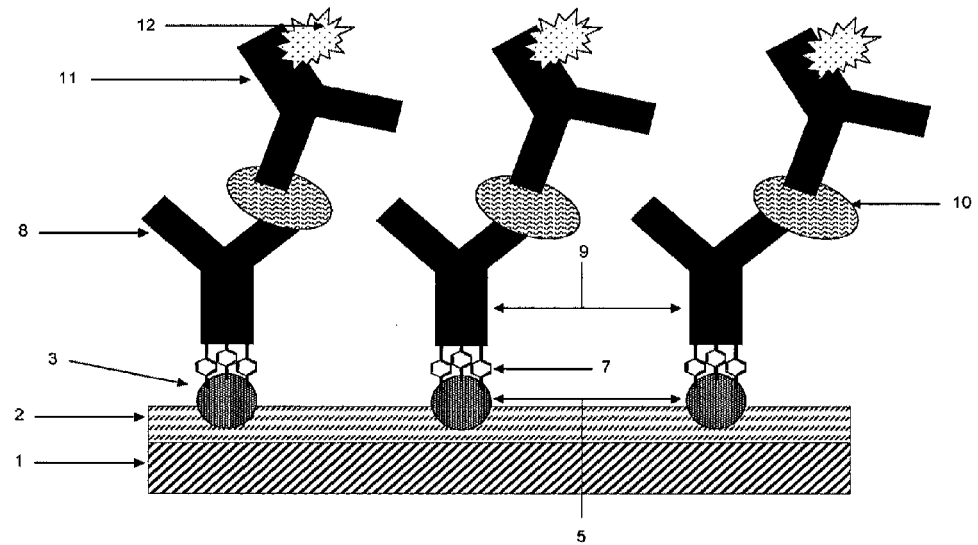

FIGS. 8(a) and (b): Illustration of multiple moieties (in these examples antibodies), attached to the nano-particle biochip substrate, which have interacted specifically with secondary bio-molecules (in this example antigens or analytes, specific to the antibody). Furthermore, primary 'labeled' antibodies have attached to the analytes (e.g. a sandwich assay). The label may be any optical or other label such as a fluorescent, luminescent, or colorimetric tag, which enables an end user to identify if, and/or what, interactions have occurred (through the use of a relevant 'reader' or 'scanner' device). FIG. 8(a) illustrates direct attachment of the moieties to the nano-particles. FIG. 8(b) illustrates attachment of the moieties to the nano-particle via small molecule linkers. Each illustrates how the nano-particle biochip substrate herein disclosed can optionally be used as a substrate for studying and interacting with bio-molecules.

Figure 9:
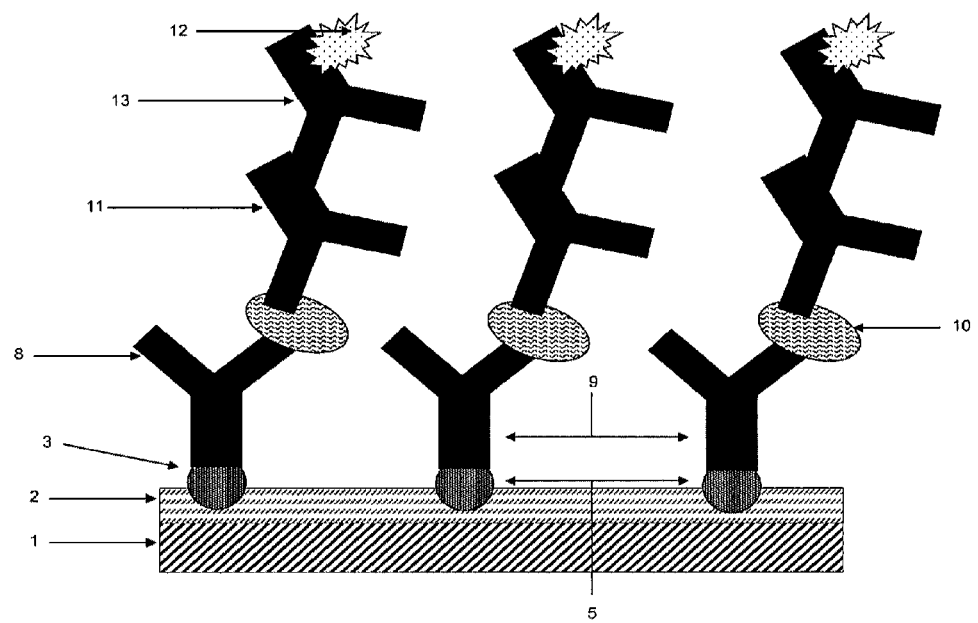
Figure 9:
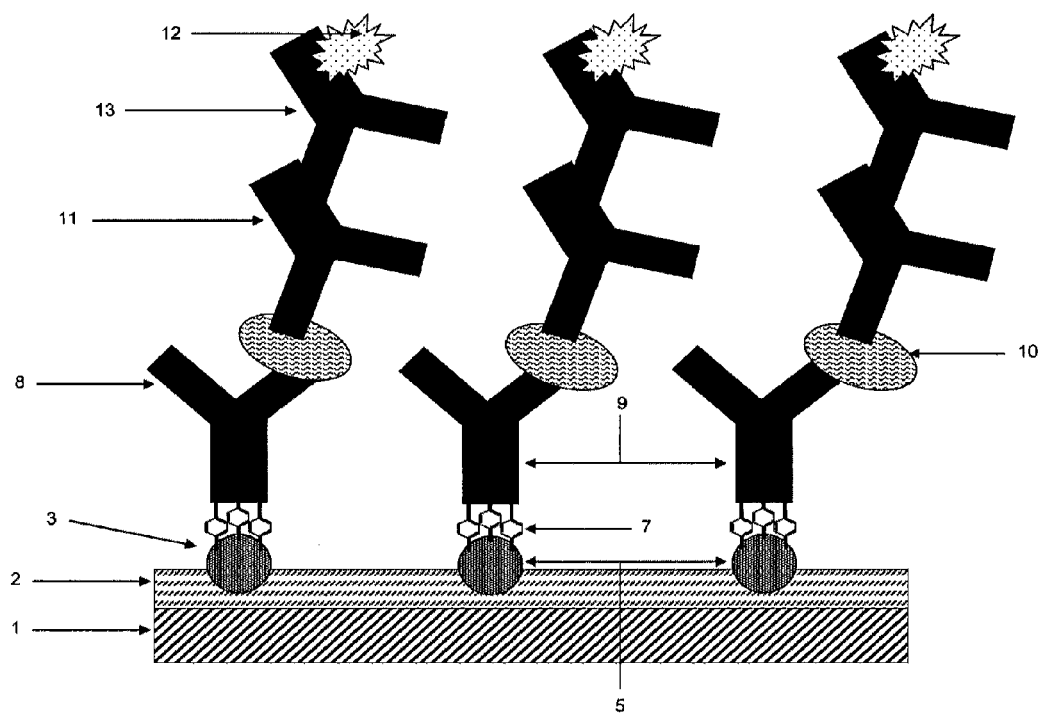

FIGS. 9(a) and (b): Illustration of an optional use of the nano-particle biochip substrate, as illustrated in FIGS. 8(a) and (b). However, in this illustration the primary probe molecules do not carry labels. Instead, secondary probe molecules carry labels (secondary labeled antibodies). FIG. 9(a) illustrates direct attachment of the moieties to the nano-particles. FIG. 9(b) illustrates attachment of the moieties to the nano-particle via small molecule linkers. Each illustrates how the nano-particle biochip substrate herein disclosed can optionally be used as a substrate for studying and interacting with bio-molecules.

Figure 10:
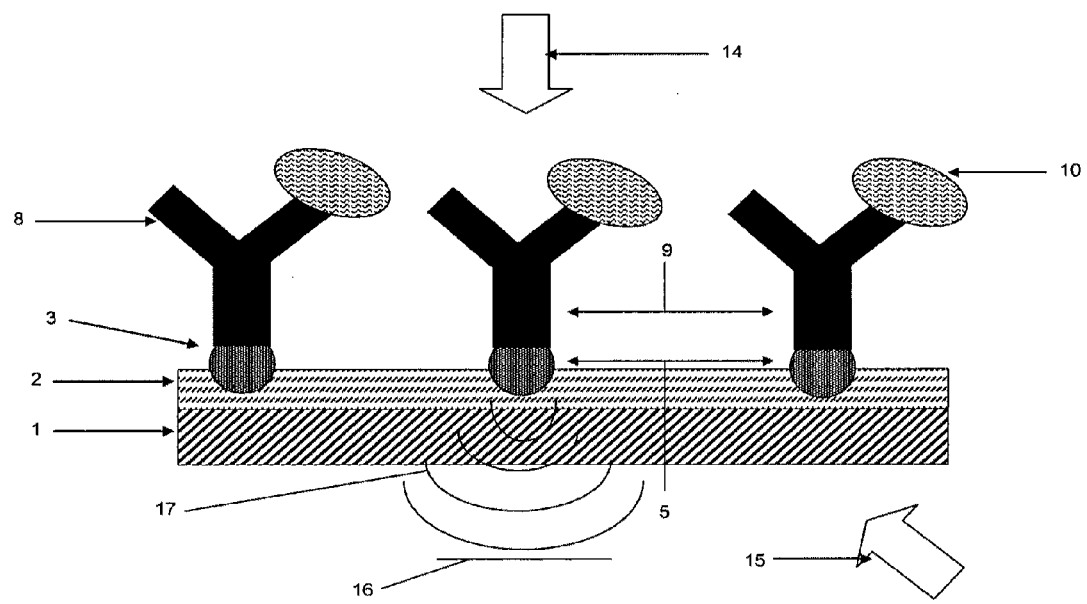
Figure 10:
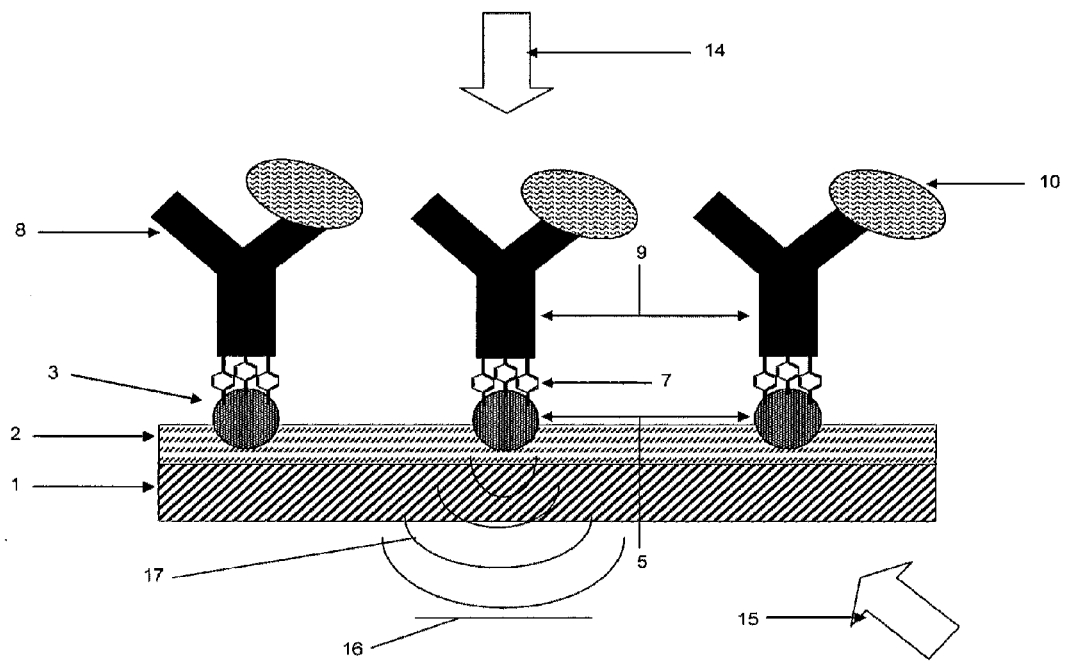

FIGS. 10(a) and (b): Illustration of the nano-particle biochip substrate being used for 'label free' detection of interaction events on its surface. In this example, the method of detecting an analytes presence is optionally through a label free optical method including, but not limited to, Surface Plasmon Resonance (SPR) in both reflection or transmission modes, or Ellipsometry. FIG. 10(a) illustrates direct attachment of the moieties to the nano-particles. FIG. 10(b) illustrates attachment of the moieties to the nano-particle via small molecule linkers. Each illustrates how the nano-particle biochip substrate herein disclosed can optionally be used as a substrate for studying and interacting with bio-molecules.

Figure 11:
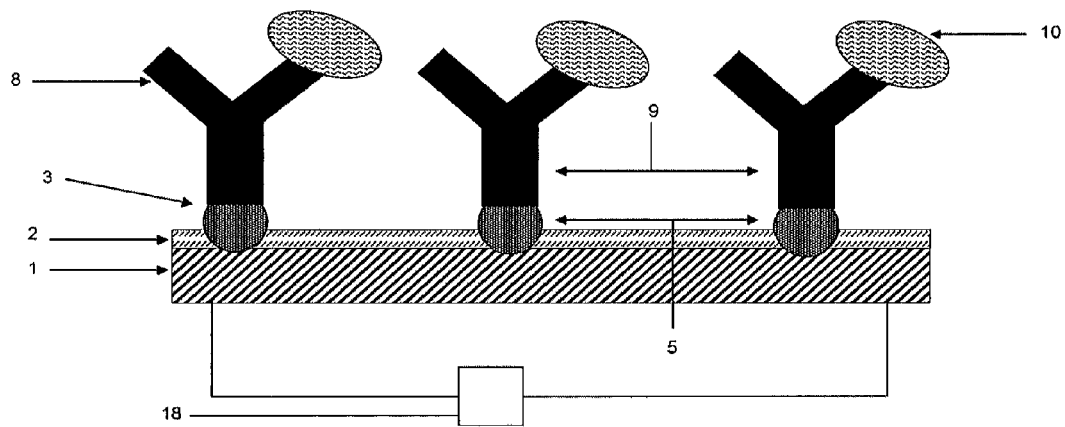

FIG. 11: Illustration of the nano-particle biochip substrate being used for 'label free' detection of interaction events on its surface. In this example, the method of detecting an analytes presence is through a label free method based on recording a shift in an electronic signal passed through the nano-particle biochip substrate. The signal being detected could include, but is not limited to, a change in resistance across the nano-particle biochip substrate, or a change in conductivity across the nano-particle biochip substrate, or a change in current across the nano-particle biochip substrate, or a change in capacitance across the nano-particle biochip substrate, or a change in voltage across the nano-particle biochip substrate, or a change in current across the nano-particle biochip substrate. Each illustrates how the nano-particle biochip substrate herein disclosed can optionally be used as a substrate for studying and interacting with bio-molecules.

Figure 12:
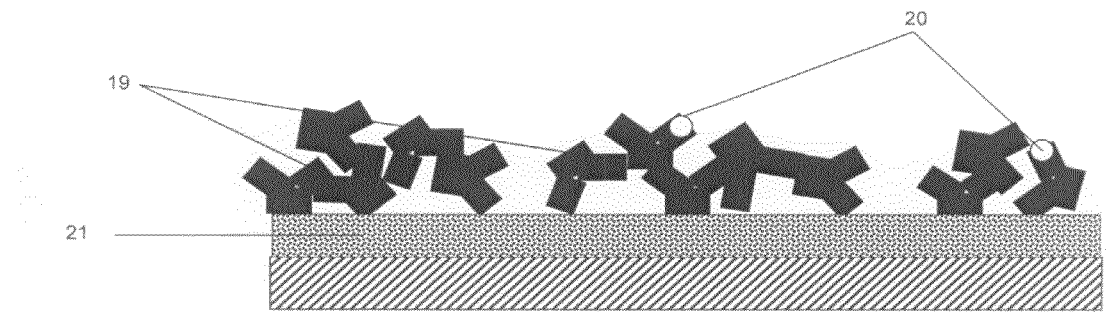
Figure 12:
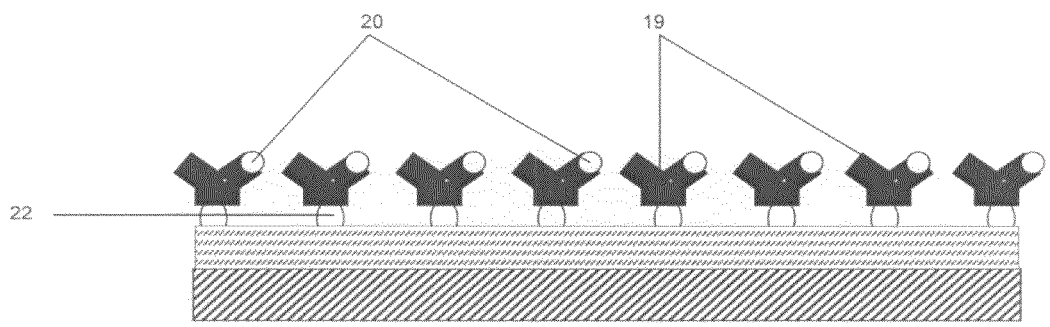

FIGS. 12(a) and (b): Illustration of an extended unit area on a biochip surface when moieties are deposited onto the surface. FIG. 12(a) illustrates an extended unit area on a surface of a 'standard' biochip substrate (NOT a nano-particle biochip substrate). Illustrated clearly is the problem of random distribution and orientation of moieties on such a surface. In this example, only one active site is readily available and one is partially available for interaction purposes (i.e. only two antibodies are left useful for the user within this unit area. Furthermore, due to the random processes involved this figure could change significantly across the surface of the biochip substrate, causing high variability). FIG. 12(b) illustrate an extended unit area on a surface of the nano-particle biochip substrate herein disclosed (the invention). Illustrated clearly is the ordered distribution and orientation of moieties on this surface. In this example, eight active sites are readily available for interaction purposes (i.e. eight antibodies are left useful for the user within this unit area). The increased density of 'useful' moieties (i.e. functional and with their active sites available for interaction), boosts the signal from a unit area on the surface, increasing the sensitivity of biochip systems the nano-particle biochip substrate is used with. Furthermore, control over the number of 'useful' moieties in any unit area boosts the consistency of biochip systems the nano-particle biochip substrate is used with, and virtually eliminates variability across the substrate, and from substrate to substrate.

Figure 13:
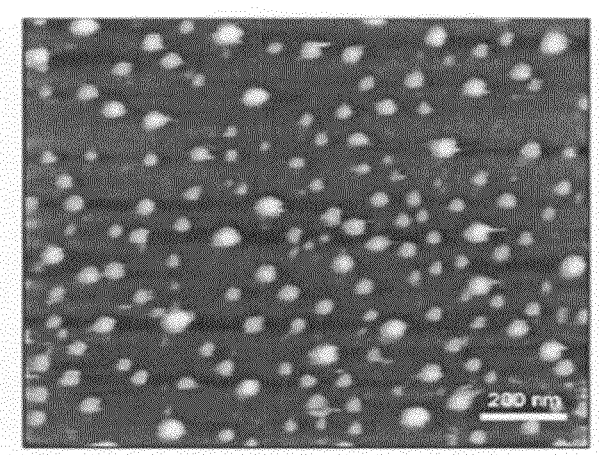

FIG. 13: An atomic Force Microscope (AFM) image of a base surface with size specific nano-particles attached to the base surface such that they protrude from the topmost surface. In this example, the size specific nano-particles were deposited in a random distribution, but the average spacing between the nano-particles (i.e. the number and density of nano-particles in the unit area shown on the image) was controlled. Subsequently, proteins were deposited in solution onto the imaged nano-particle biochip substrate, the solution was left to incubate with the nano-particle biochip substrate (NBS), prior to being washed off, and the NBS imaged in the AFM. Thus, clearly visible in the image are large 'blobs', which are the protein and nano-particle pairings, alongside small 'blobs' which are the nano-particles.

DETAILED DESCRIPTION

Background Research

Research conducted at the Nano Physics Research Laboratory at the University of Birmingham in the UK, has shown how inorganic 'nano-scale' clusters can be embedded into or pinned onto a flat surface. The cluster patterned surfaces have been shown to be stable at temperatures up to 350° C. (see published technical papers: 1. C. Xirouchaki and R. E. Palmer: *Deposition of size-selected metal clusters generated by magnetron sputtering and gas condensation: a progress review.* 2. S. Pratontep, P. Preece, C. Xirouchaki and R. E. Palmer: *Scaling Relations for Implantation of Size-Selected Au, Ag, and Si Clusters into Graphite.* 3. M. Couillard, S. Pratontep, and R. E. Palmer: *Metastable ordered arrays of size-selected Ag cluster on graphite.*).

It has been shown in further research conducted at the Nano Physics Research Laboratory at the University of Birmingham in the UK, that proteins may be anchored to gold clusters embedded into a surface. (See published technical papers: 1. Collins, J. A., C. Xirouchaki, R. E. Palmer, J. K. Heath, and C. H. Jones: *Clusters for biology: immobilisation of proteins by size-selected metal clusters.* 2. Prisco, U., C. Leung, C. Xirouchaki, C. H. Jones, J. K. Heath, and R. E. Palmer: *Residue-specific immobilisation of protein molecules by size-selected clusters.* 3. Leung, C., C. Xirouchaki, N. Berovic, and R. E. Palmer: "*Immobilization of protein molecules by size-selected metal clusters on surfaces,*"). It has been further shown that the proteins anchored to the gold clusters show a higher propensity to retain their original function than would be expected were the proteins to be anchored to an extended flat surface (see published technical papers: Prisco, U., C. Leung, C. Xirouchaki, C. H. Jones, J. K. Heath, and R. E. Palmer, *Residue-specific immobilisation of protein molecules by size-selected clusters.*). Further, research at the Federation de Recherche et Laboratoire de Physique du Solide, ESPCI, Paris, France, alongside that from the Oak Ridge National Laboratory, has shown that nano-scale metallic clusters (nano-particles) can be used to amplify the fluorescent signal on a biochip device (see published technical papers: 1. E. Fort, S. Leveque-Fort, E. Le Moal, J. P. Lacharme, M. P. Fontaine-Aupart and C. Ricolleau: *Metallic nano-structured substrates for enhanced fluorescence bio-analysis*. 2. Fei Yan, M. Wabuyele, G. Griffin, T. Vo-Dihn: *Metallic nanostructures for plasmonic sensors using surface-enhanced fluorescence and Raman detection*).

Controlling the physical and chemical structure of a surface at the nano-scale is a capability sought after in many fields. One of the most relevant fields for such a capability is within the many applications of biochips. Indeed, precise control over the physical and chemical properties of a biochip substrate at the scale of the bio-molecules or other moieties being attached or interacted with (at the nano-scale) would enable significant improvements in the performance of most biochip systems. The current invention offers a nano-particle biochip substrate that offers such control over the nano-scale physical and chemical structure of a surface.

The current invention comprises a number of different embodiments focused on nano-particle biochip substrates (NBS's) and uses thereof. As will be apparent upon examination of the present specification, figures, and claims, NBS's present improved and unique aspects that are beneficial in a wide variety of applications, including but not limited to, drug discovery, drug development, protein R&D, diagnostics, catalysis, biological or chemical sensors, as well as generic screening tools, assaying tools (e.g. microarrays) etc. It will be appreciated that the NBS's herein are sometimes referred to as "cluster biochip substrates;" some illustrations, examples, etc. herein are described in terms of clusters.

A common factor in the embodiments is the special physical and chemical surface structure of NBS's, typically a plurality of nano-particles patterned at a chosen density onto a surface. In certain embodiments, NBS's are functionalized with one or more moiety (either through direct attachment to the nano-particle or via a linker molecule). In most aspects herein, it is thought that the benefits detailed accrue from the unique surface structure of the NBS's, and from the associated greater concentration of 'useful' units per unit area or volume on the substrate ('useful', meaning it has retained its original function and its active site is available for interaction with further moieties), but the various embodiments herein are not necessarily limited by such theory in their construction, use, or application.

In certain embodiments of this invention, nano-particles are selected for nano-particle size to ensure that only one moiety (e.g. a bio-molecule such as a protein) is directly attached to each nano-particle (additional moieties can subsequently attach to the nano-particle/bio-molecule combination). Alternatively, the nano-particle size can be selected to enable the direct binding of multiple moieties onto its surface; to influence the orientation of the selected moiety of interest attached to the nano-particle; to help retain the original function and structure of the moiety of interest (e.g., in the case of a bio-molecule) as attached to the nano-particle; to assist in the amplification of fluorescent detection signals; to assist in the enhancement of Surface Plasmon Resonance (SPR) detection; to function as both an anchoring point for moieties and as part of a labeled or label free signal generating system, recording primary, secondary or subsequent attachment of moieties of interest; or a combination of the foregoing.

In addition, nano-particles are selected for material type (material of which they are comprised) to influence the orientation of the selected bio-molecule attached to the nano-particle; to help retain the original function and structure of the bio-molecules deposited onto the nano-particle; to assist in the amplification of fluorescent detection signals; to assist in the enhancement of Surface Plasmon Resonance (SPR) detection; to function as both an anchoring point for bio-molecules and as part of a labeled or label free signal generating system, recording primary or secondary or subsequent attachment of biological molecules; or a combination of the foregoing.

In certain embodiments, the spacing and/or density of the nano-particles on the surface is controlled to: (a) Control the spacing of bio-molecules on the surface; and/or (b) Control the number of bio-molecules on the surface; and/or (c) optimize the number and spacing of bio-molecules on the surface; (d) Retain consistency across the surface and from surface to surface; and/or (e) Reduce undesired interactions between bio-molecules on the surface.

The background surface onto/into which the nano-particle are attached is chosen to: (a) Reduce the background 'noise' from the surface; and/or (b) Reduce undesired binding of bio-molecules to the background surface; and/or (c) Help retain the original function and structure of the bio-molecules deposited onto the surface for subsequent attachment to the nano-particles or nano-particle/moiety pairing.

The nano-particle size suitable for various embodiments of the present invention ranges from a cross-sectional dimension (e.g., diameter) of approximately 0.1 nm to about 50 nm.

In some aspects, the current invention comprises nano-particles or nano-scale clusters attached to a first or second surface ('attached' herein means pinned, embedded or otherwise secured onto or into a surface, with part of the nano-particle protruding from that surface, such that they are secured in one position and do not substantially move under normal conditions of use for biochip substrates), to act as 'anchoring' points for various moieties such as biological molecules, catalysts etc. (biological molecules (bio-molecules) include proteins, peptides, lectins, genes, DNA, cell lysates and other small bio-molecules). It should be noted that herein, the term "surface bearing nano-particles" can be used interchangeably with "nano-particle attached to a surface". Nano-particles or clusters are herein used to refer to clusters or particles of a specific material, with a substantially uniform cross section and average cross sectional diameter ranging between 0.1 nm and 50 nm, and in particular embodiments, between 0.5 nm and 40 nm, or between 1 nm and 30 nm, or between 2 nm and 20 nm, or between 3 nm and 10 nm, or between 1 nm and 10 nm or between 3 nm and 7 nm. In some embodiments the nano-particles attached to the first or second surface are selected for their size prior to attachment to the chosen surface, or their size is controlled if the nano-particles are grown on the chosen surface. In other embodiments a range of nano-particle sizes are attached to the chosen surface. The surface having nano-particles attached thereto herein described, is referred to as the 'nano-particle biochip substrate' or 'NBS'.

In other aspects, the current invention comprises a nano-particle biochip to substrate with small molecule 'linkers' attached to the nano-particles attached to the first or second surface. The term 'linkers' as used herein means small molecules which can be attached at one end, via chemical or other bonding mechanisms, to one surface, e.g. the nano-particles, such that they can subsequently be attached at their other end, via chemical or other bonding mechanisms, to a moiety of choice, e.g. bio-molecule or catalysts. In other words they link the nano-particle to a moiety via a chosen bonding mechanism. These linkers can be chemically or physically absorbed at one end onto the nano-particles before or after the nano-particles are attached to the first or second surface, with the other functional end free for the subsequent bio-molecule or catalysts attachment. In some embodiments, the chemical linkers have an average length ranging between 0.1 nm and 50 nm, and in particular embodiments between 0.2 nm and 40 nm, or between 0.3 nm and 30 nm, or between 0.4 nm and 20 nm, or between 0.5 nm and 10 nm, or between 0.5 nm and 5 nm, or between 0.5 nm and 1 nm. Examples of such linkers include, but are not limited to, small molecules with carboxyl or amine groups on one functional end, and sulphur groups on the other, e.g. general chemical structures such as, HS—R—COOH, or HS—R—$NH_2$, or (HS—$R_1$)$_n$—$R_2$—COOH, or (HS—$R_1$)$_n$—$R_2$—$NH_2$; where the R, R1, and R2 can be any alkanes, or arenes, or other suitable chemical group. Further, more specific examples include, but are not limited to, 4-mercaptobenzoic acid (HS—$C_6H_4$—COOH), cysteamine (HS—$CH_2$—$CH_2$—$NH_2$), (HS—$(CH_2)_3)_2$—$C_6H_4$—COOH, (HS—$(CH_2)_4$—O)$_2$—$C_6H_4$—$(OCH_2)_{10}$—COOH, and (HS—$(CH_2)_4$—O)$_2$—$C_6H_4$—$(OCH_2)_{20}$—$NH_2$. In some embodiments, the linker molecules include, but are not limited to, molecules that have one functional end that can be chemically or physically absorbed onto an amino acid, such as any of the amino acids within a protein (e.g., Alanine, Arginine, Asparagine, Aspartic acid, Cysteine, Glutamic acid, Glutamine, Glycine, Histidine, Isoleucine, Leucine, Lysine, Methionine, Phenylalanine, Proline, Serine, Threonine, Tryptophan, Tyrosine, Valine), and another functional end that can be chemically or physically absorbed direct onto the nano-particles (e.g., gold, silver, silicon, platinum, iron, copper, phosphorous, palladium, aluminum, cesium, nickel, tin, various oxides, etc. or alloys thereof).

In other aspects, the current invention relates a nano-particle biochip, which is a nano-particle biochip substrate with moieties of interest (bio-molecules, catalysts etc.) attached, directly or indirectly, to the nano-particles attached to the first or second surface. In some embodiments the moieties attach to the nano-particles via linkers attached to the nano-particles. In other embodiments, the moieties will attach directly to the nano-particles.

Nano-particles as used herein refers to more than one, and typically three or more, metal, alloy, semiconductor, magnetic, or other atoms, coupled to one another by metal-type or ionic bonds. Nano-particles are intermediate in size between single atoms and colloidal materials. Nano-particles made in accordance with the present invention are also referred to herein as "clusters". This indicates that the cross sectional diameter of each such nano-particle is typically between 0.1 nm and 50 nm, or between 0.5 nm and 40 nm, or between 1 nm and 30 nm, or between 2 nm and 20 nm, or between 3 nm and 10 nm. The nano-particles will approach spherical in most embodiments, while in others they will alternative shapes formed by a collection of atoms. In all embodiments the cross sectional diameter of a nano-particles is herein defined as: The average of three cross sections orthogonal to each other and each passing through the nano-particles center of mass.

In various embodiments of the invention, the nano-particles may include, but are not limited to, gold; silver; platinum; copper; phosphorus; nickel; aluminum; cesium; palladium; carbon; magnesium; silicon; titanium; chromium; manganese; iron; cobalt; zinc; gallium; germanium; selenium; krypton; rubidium; strontium; zirconium; cadmium; tin; xenon; barium; tantalum; tungsten; iridium; thallium; lead; bismuth; polonium; radium; thorium; uranium; plutonium; americium; californium; einsteinium; fermium; nobelium; rutherfordium; bohrium; teflon; an oxide, an inorganic compound, or a mixture, an alloy or a combination of any of the foregoing.

In certain embodiments of the invention, the nano-particles can be selected for their size before attachment to the surface, or their size can be controlled if the nano-particles are grown on the surface, such that the nano-particles on the surface have substantially the same average cross-sectional diameters. In these embodiments the nano-particles attached to the surface are known as 'size selected' nano-particles; and the average cross-sectional diameters of each nano-particle on the surface are selected with a variance of under 1%, or under 2%, or under 3%, or under 4%, or under 5%, or under 6%, or under 7%, or under 8%, or under 9%, or under 10%, or under 12%, or under 14%, or under 16%, or under 18%, or under 20%, or under 25%, or under 30%, or under 40%, or under 50%. A variation in the average cross-sectional diameter of the nano-particles on a surface of above 50% is not considered size specific.

In some embodiments of this invention, the nano-particles are attached to a substrate in predetermined patterns, or in a random distribution within predetermined surface regions. The resultant surface can provide an organized array of immobilization sites (anchoring sites) for moieties (including bio-molecules, bio-molecule linker molecules, catalysts). If the nano-particle biochip substrate surface is divided into regions on the surface the nano-particles within each region may, optionally, be size selected. In some embodiments the nano-particles in one region will be a different average size to the nano-particles in a different region, or each region may contain nano-particles size selected for the same size.

In other embodiments, the nano-particles are not size selected, and a random range of nano-particle sizes is present on the surface.

In other embodiments of the invention, each nano-particle may be embedded in the nano-particle biochip substrate to a predetermined depth, such that the surface areas presented to a linker or moiety for attachment is controllable.

In some aspects, the invention comprises a biochip comprising a base surface with at least a first surface; and at least one nano-particle of a specific material (typically substantially more than 1 nano-particle) attached to the first surface (or optionally the second surface), but elevated with respect to the surface. For example, a standard 1'×3' silicon or glass microscope slide could be used as the first surface, with a thin layer of a biologically inert polymer coated on top being used as the second surface (collectively termed the base surface), onto which the nano-particles are deposited and attached (e.g. pinned, embedded, grown). The slide dimensions are not critical and can be varied as appropriate. Additionally, the use of 'wells' or 'pads' to define specific regions on the slides surface can optionally be used.

The base surface can be made of a wide variety of materials, including but not limited to: glass; chemically treated glass; silicon; mica; graphine; graphite; aldehyde; epoxy; strepavidin; biotin; silane; agarose; dextran; diamond; magnetic tape; at least one polymer, such as polyethylene glycol (PEG) or oligoethylene glycol (OEG); a carbon nano tube; gold; silver; copper; phosphorous; nickel; carbon; magnesium; titanium; iron; zinc; selenium; cadmium; tin; tungsten; lead; teflon; nitrocellulose; lipids; a hydrogel; a plastic; or rubber.

The base surface can be made in a wide variety of formats and dimensions, including but not limited to those listed below.

In some embodiments, the base surface can be a standard 1'×3' micro-array type slide, suitable for use within a wide variety of biochip applications. In other embodiments, the base surface could be a 3×5' 96 well plate substrate, a 384 well plate substrate, or a 1,536 well plate substrates, or any alternate 3'×5' well plate format. In other embodiments the dimensions of the base surface may be non-standard and be designed to fit into a specific biochip reader/scanner device.

In some embodiments, the base surface could be the inside of a micro-channel (micro-channel is used herein to describe a micron or nano scale channel in a biochip system, used as a means to channel samples, reagents and other such solutions or moieties of interest, and to observe the resultant mixing and/or other effects), into which nano-particles are attached; or, the nano-particles could be attached onto/into a 'rod' which would be inserted into a micro-channel to achieve the same effect.

In other embodiments, the base surface could be spherical or otherwise shaped. For example, the base onto/into which the nano-particles were attached can be beads, or other spherical surfaces compatible with bead based biochip systems.

In other embodiments, the base surface can be a substrate designed for use with a Mass Spectrometry system, such as a MALDI or SELDI system.

In other embodiments, the base surface can be a substrate designed for Surface Plasmon Resonance biochip systems, or a substrate designed for ellipsometry based biochip systems, a substrate designed for Fluorescence Resonance Energy Transfer (FRET) based biochip systems, or a substrate designed for any alternative type of detection method, arraying machine, array scanner, or biochip system.

As described herein, a nano-particle biochip substrate has the advantages that it helps to:
(a) retain the original function of complex bio-molecules (e.g. proteins) when they are anchored to a surface;
(b) influence the bio-molecules' orientation;
(c) control the spacing and density of the bio-molecules to optimize the signal from any unit area on the surface of a biochip;
(d) ensure only one bio-molecule is directly attached to each nano-particle, thus enabling precise control over the number of bio-molecules in any unit area on the surface of a biochip, virtually eliminating variability problems;
(e) amplify fluorescent reader signals from introduced fluorescent tags;
(f) enhance SPR detection methods; and
(g) facilitate alternative label free detection methods;

In addition, the nano-particle biochip substrate can integrate across (is useful in) virtually all biochip substrate formats, including but not limited to, substrates for fluorescent or luminescent assays, substrates incorporating micro-channels, lab on a chip type substrates, 1'×3' micro-array slide substrate, 3'×5' well plate substrate, 96 well plate substrate, 384 well plate substrate, 1,536 well plate substrates, substrates for Mass Spectrometry, substrate for Surface Plasmon Resonance, substrates for ellipsometry, substrates for imaging ellipsometry, substrates for Fluorescence Resonance Energy Transfer (FRET), substrates for colorometric assay systems, etc.

The unique and novel properties of the 'NBS' thus described, are achieved through control over a combination of one or more of the following parameters: The nano-particle size, the nano-particle material, the distance of protrusion of the nano-particle from the background surface, the average separation between nano-particles in a unit area on the surface (the average density), the total number of nano-particles in a unit area on the surface, the nano-particles stability on the surface, and the background (base) surface itself. These parameters may be adjusted to affect the types of moieties (bio-molecules) captured thereby, and the specific applications the biochip substrates are used for, as discussed below:
1. The nano-particle size. The size of the cluster is relevant for the following reasons:

(a) By selecting the size of the cluster, one is able to influence which residue a bio-molecule of interest the nano-particle 'favors'. A smaller nano-particle size is more likely to bind to the smaller residues, whereas the larger nano-particle sizes bind to the larger residues. Accordingly, one is able to influence the orientation of the bio-molecule (e.g. protein) through specific size selection.
(b) By selecting the size of the nano-particle, one is able to substantially ensure that only one moiety (bio-molecule, e.g. protein, or catalyst) attaches directly to the nano-particle. Moreover, particular nano-particle sizes may be selected to optimally bind particular bio-molecule types and bio-molecule sizes. Note, once the first moiety has directly bound to the nano-particle (optionally via linker molecules), subsequent moieties can then bind to the nano-particle/moiety pairing.
(c) Where desirable for certain applications, one is able to select the nano-particle size to substantially ensure that multiple moieties attach directly to the nano-particle surface (e.g., 2 moieties per nano-particle, or 3, etc.).
(d) By selecting a size specific nano-particle one is also able to help retain the original function of bio-molecules (especially relevant for proteins). Typically the smaller the contact point between the surface and the protein the more likely the protein is to retain its original structure and function. Accordingly, the nano-particle sizes may be optimized to ensure immobilization while also minimizing the area of contact with the bio-molecule (e.g. protein).
(e) By selecting a specific sized nano-particle one may also be able to assist in the amplification of fluorescent 'tags', when located at an appropriate distance from the nano-particle. For example, in some embodiments, the optimal size of the nano-particle for this purpose would be in the range of 1 to 50 nm, and would be dependant on the average distance from the fluorescent tag. Accordingly, the nano-particle size can be controlled to effectively act as signal boosters in a fluorescent detection system.
(f) By selecting a specific size of nano-particle, surface plasmon resonance signal from the nano-particle sites can be enhanced. The optimal size for this application in some embodiments hereof, is about 10 nm or greater.

2. The nano-particle material. The material used to form the nano-particles influences how certain bio-molecules (e.g. proteins) interact and anchor themselves to the nano-particle sites. This is due to the type of chemical bond each different material can make with different bio-molecule types. For example; the five surface cysteine residues on the protein 'Oncostatin M' (one of which is 'free' and the other four of which form 'disulphide bridges') are able to link directly to a gold nano-particle via a Thiol bond. Accordingly gold is a very good material to bind Onconstatin M (indeed gold is a good material for a large number of proteins for this type of bonding capacity). Other suitable materials, such as silver, platinum, copper, silicon, phosphorous, nickel, aluminum, cesium, and many others known to those skilled in the art, may be useful for bonding to other bio-molecules. Additionally, the nano-particle material can be selected to bind to a 'linker' molecule which in turn would bind to a bio-molecule.

3. Nano-particle protrusion. The protrusion from the surface is relevant because it helps the bio-molecules retain their function. This is especially relevant for proteins, which are very prone to denaturing (changing their structure and function) when coming into contact with a surface. By raising the protein above the surface on a 'nano-scale' structure (our nano-particle sites), we are able to simulate more readily its native environment and substantially increase its chances of retaining its original structure and function. Furthermore, by controlling the depth of the nano-particle in the background surface, the surface area available to interact with moieties is further controlled.

4. The average separation between nano-particles in a unit area on the surface. By controlling the average separation/distance between nano-particles in a unit area on the base surface, it is possible to optimally space the nano-particles such that when moieties are attached, the moieties have freedom of movement without being hindered by a nearest neighbor. This is especially relevant for proteins, which may denature when they come into contact with other bio-molecules, or stick to them to form protein islands. Furthermore, controlling the spacing, ensures that moieties are optimally spaced to ensure they do not hinder each other. This makes it possible to ensure they are close enough to provide an optimal density of moieties on the surface.

5. The total number of nano-particles in a unit area on the surface. By controlling the number of nano-particles in any unit area on the base surface, Applicant was able to in turn control the number of moieties that will attach to the substrate in any unit area. Furthermore, in conjunction with some of the other parameters/features of the NBS mentioned herein it is possible to control the number of 'useful' moieties attached to a substrate in any unit area (useful meaning it has retained its original function and its active site is available for interaction with further moieties). As a result, it is possible to virtually eliminate inter-substrate and substrate to substrate variability, for a wide range of biochip applications.

6. Nano-particle Stability. The stability of the nano-particles on the background surface enables that substrates will remain consistent in their performance over time, and can be used in all conditions familiar to those skilled in the art of biochip use (e.g. with washing solutions, blocking solutions, heating, cooling, agitating, etc.).

These and other objects and features of the invention will become more fully apparent when the following detailed description is read in conjunction with the accompanying figures.

I) Characteristics of Nano-Particle Biochip Substrates (NBS's)

A 'nano-particle biochip substrate (NBS)' herein corresponds to a surface (or substrate) comprising at least a first surface (FIG. 1(a)), with one, or a plurality of, nano-particles (clusters) attached to the first surface (attached is used herein to refer to a nano-particle or cluster pinned, embedded, grown on, or otherwise secured to a surface, such that part of the nano-particle is available for its intended function(s) (e.g., to interact with/attach a moiety of interest). As a result, the nano-particle protrudes above (from) the surface, is in a cavity in the surface or is positioned at the same levels as the surface. FIG. 2(a) and FIG. 3). In some embodiments, the nano-particles will be roughly spherical, and can comprise an average cross sectional diameter of about 0.1 nm or less, to at least 50 nm, from about 0.5 nm or less to at least 40 nm, from about 1 nm or less to at least 30 nm, from about 2.5 nm or less to at least 20 nm, from about 2.5 nm or less to at least 10 nm.

In some embodiments, the first surface will have a second surface layered on top of the first surface, with one, or a plurality of, nano-particles (clusters) being attached to the second surface (FIG. 1(b)). In other embodiments, the first surface will have a second surface layered on top of said first surface, with one, or a plurality of, nano-particles (clusters) penetrating through the second surface to come into contact with the first surface. However, the second surface will be sufficiently thin to still enable the nano-particle to protrude from the second surface, i.e. the topmost surface (FIG. 2(b)).

In all such embodiments the nano-particles can be attached to the surface in random or controlled patterns, and the average spacing between each nano-particle in any unit area on the surface, whether in a random distribution or a controlled distribution can be from about 1 nm or less to at least 200 nm, 1 nm or less to at least 100 nm, from about 5 nm or less to at least 90 nm, from about 10 nm or less to at least 80 nm, from about 15 nm or less to at least 70 nm, from about 20 nm or less to at least 60 nm, from about 25 nm or less to at least 50 nm, from about 30 nm to at least 45 nm, from about 30 nm to at least 40 nm (FIG. 3).

In such embodiments the nano-particles can comprise a variety of non-biological materials, including but not limited to, metals, alloys, semiconductors, polymers, magnets, etc. Examples of such nano-particle materials include, but are not limited to, gold; silver; platinum; copper; phosphorus; nickel; aluminum; cesium; palladium; carbon; magnesium; silicon; titanium; chromium; manganese; iron; cobalt; zinc; gallium; germanium; selenium; krypton; rubidium; strontium; zirconium; cadmium; tin; xenon; barium; tantalum; tungsten; iridium; thallium; lead; bismuth; polonium; radium; thorium; uranium; plutonium; americium; californium; einsteinium; fermium; nobelium; rutherfordium; bohrium; teflon; an oxide, an inorganic compound, or a mixture, an alloy or a combination of any of the foregoing.

In such embodiments, the first surface (FIG. 1(a)), and where present, the second surface (FIG. 1(b)), can comprise one or more of a variety of materials including but not limited to, glass; chemically treated glass; silicon; mica; graphine; graphite; aldehyde; epoxy; strepavidin; biotin; silane; agarose; dextran; diamond; magnetic tape; at least one polymer, such as polyethylene glycol (PEG) or oligoethylene glycol (OEG); a carbon nano tube; gold; silver; copper; phosphorous; nickel; carbon; magnesium; titanium; iron; zinc; selenium; cadmium; tin; tungsten; lead; teflon; nitrocellulose; lipids; a hydrogel; a plastic; or rubber.

In some embodiments, one or more nano-particles is coated with one or more linker molecule, or has one or more linker molecule attached to its surface ('linker' herein means a small molecule which can be attached at one end, via chemical or other bonding mechanisms, to one surface, e.g. the nano-particles, such that they can subsequently be attached at their other end, via chemical or other bonding mechanisms, to a moiety of interest, e.g. bio-molecule or catalysts. In other words they link the nano-particle to a moiety of interest via a chosen bonding mechanism). These linkers can be coated or otherwise deposited onto the nano-particles before or after the nano-particles are attached to the first or second surface (FIGS. 4(a) and (b)).

In some embodiments described herein, one or more nano-particles is functionalized with one or more moiety of interest (including, but not limited to, bio-molecules, catalysts, etc.), either through direct attachment of the moiety to the nano-particle surface, or attachment of the moiety to the nano-particle surface via a linker molecule (FIGS. 5(a) and (b), and FIGS. 6(a) and (b)). However, it will also be noted that the current invention is not specifically limited by the composition of the nano-particles, the composition of the linkers or the composition of first or second surface onto/into which the nano-particles are attached, unless otherwise noted.

Thus, as an illustrative, but not limiting, example, FIGS. 6(a) and (b) and FIG. 12(b) present schematic representations of a nano-particle biochip substrate of the invention. FIG. 12(a) on the other hand, represents a typical (non nano-particle patterned surface) biochip substrate comprising a finite number of 'useful' units, in this example antibodies. 'Useful' units means bio-molecules that have retained their original function (Substantially the same function as that it exhibits in its native environment) and have the 'active sites' of interest to the end user (for interacting with compounds, biomarkers, etc.) presented for interaction with subsequent molecules. As can be seen, only a certain number of useful units fit within any unit area on the substrate (1 or 2 in this example). FIG. 12(b), however, presents one possible embodiment of the current invention. The substrate in FIG. 12(b) presents the same unit area as that of FIG. 12(a), but because of the nano-particle structured surface, the number of useful units is greatly increased (8 in this example). FIG. 13 displays an atomic force microscope image nano-particle patterned substrate following incubation with a solution containing proteins. It will be noted that the number, size, material, chemical functionality and distribution of the nano-particles, coupled to the background surface onto/into which the nano-particles are attached, allows ample opportunity for multiple substrate physical formats, multiple substrate chemical formats, multiple substrate functionality, etc. and thus multiple applications of such a substrate. Again, it is to be emphasized that such examples are merely to illustrate the myriad possible embodiments of the current invention.

The various embodiments of the current invention are adaptable to, and useful for, a great number of different applications. For example, drug discovery, drug development, protein R&D, diagnostics, catalysis, biological or chemical sensors, as well as generic screening tools, assaying tools (e.g. microarrays) etc.

As explained in greater detail below, an aspect of the current invention is its use in micro-arrays (e.g. protein assays) where, typically, slides of glass; chemically treated glass; silicon; mica; graphine; graphite; aldehyde; epoxy; strepavidin; biotin; silane; agarose; dextran; diamond; magnetic tape; at least one polymer, such as polyethylene glycol (PEG) or oligoethylene glycol (OEG); a carbon nano tube; gold; silver; copper; phosphorous; nickel; carbon; magnesium; titanium; iron; zinc; selenium; cadmium; tin; tungsten; lead; teflon; nitrocellulose; lipids; a hydrogel; a plastic; or rubber, etc. are used. In the current invention, by coating a surface with nano-particles and then spotting or arranging the array on the coated surface, the 'useful' surface area density, and thus sensitivity, can be increased dramatically without sacrificing hybridization time (as would occur with tortuous path porous coatings, or extended surface area substrates). Furthermore, the variability from spot to spot, and slide to slide can be virtually eliminated. Examined in more detail below, are some other beneficial uses of various embodiments of the current invention.

Through optional control over one or more, and sometimes all, of the following parameters: The nano-particle size, the nano-particle material, the distance of protrusion of the nano-particle from the background surface, the average separation between nano-particles in a unit area on the surface (i.e. the average density), the total number of nano-particles in a unit area on the surface, the nano-particles stability on the surface, and the background (base) surface itself the NBS herein disclosed facilitates one or more of the following performance improvements to biochip systems: (a) The sensitivity of a biochip system is greatly increased due to the optimized number of 'useful' moieties (useful meaning it has retained its original function and its active site is available for interaction with further moieties) in any unit area, coupled to a low noise background surface; (b) The consistency of a biochip system is enhanced and the variability from area to area on the substrate surface, or from substrate to substrate is virtually eliminated, due to the accurate control over the number and average spacing of the nano-particles on the substrate. Thus controlling the number and spacing of 'useful' moieties on the surface; (c) The dynamic range of a biochip system is increased, due to a better sensitivity and well controlled saturation point (when all nano-particles are in use); (d) Significantly improved flexibility and transferability of data from system to system, due to both the compatibility of the NBS to be integrated into virtually any format, and the control capable over performance variability from substrate to substrate, even if the substrates are based around different formats (industry 'standards' can be implemented based around the number of useful moieties available in any unit area on a substrate regardless of the format).

As will be appreciated by those of skill in the art, many aspects of the current invention are variable in addition to the parameters previously highlighted (e.g., surface chemistries, linkers on the nano-particles, substrate physical format, as well as nano-particle size, the nano-particle material, the distance of protrusion of the nano-particle from the background surface, the average separation between nano-particles in a unit area on the surface (the average density), the total number of nano-particles in a unit area on the surface, the nano-particle stability on the surface, and the background (base) surface itself etc.). Specific illustration of various modifications, herein, should therefore not be taken as limiting the current invention. Furthermore, a variety of methods can be employed to bring the nano-particles in contact with surfaces. Additionally, while many embodiments herein comprise nano-particles that are specifically functionalized in one or more ways, e.g., through attachment of moieties and/or linkers to the nano-particles, other embodiments comprise nano-particles which are not functionalized. For example, some nano-particle biochip substrates of the invention can comprise nano-particles that optionally may not be functionalized to particular analytes to be screened (i.e. the nano-particles are left to interact with the bio-molecule mixture of interest in their natural state, with no linker or moiety attached). Analytes include, but are not limited to: organic molecules, inorganic molecules, metals, ceramics, proteins, peptides, polypeptides, nucleic acids, nucleic acid analogs, metallo-proteins, chemical catalysts, metallic groups, antibodies, cells, ions, ligands, substrates, receptors, biotin, hydrophobic moieties, alkyl chains, phenyl groups, adhesive enhancing groups, co-factors, etc.

II) Nano-Particles and Construction of Nano-Particle Patterned Surfaces

In typical embodiments of the invention, the surfaces to which (onto, into which) nano-particles are attached) and the nano-particles themselves can comprise any number of materials. The actual composition of the surfaces and the nano-particles is based upon a number of possible factors. Such factors can include, for example, the intended use of the NBS, the conditions under which they will be used (e.g., temperature, pH, presence of light, atmosphere, etc.), the reactions for which they will be used (e.g., bio-assays, high throughput screens, catalysis, diagnostics, bio or chemical sensors etc.), the durability of the surfaces and the cost, etc.

As explained more fully below, some possible materials used to construct the nano-particles herein include, but are not limited to: gold; silver; platinum; copper; phosphorus; nickel; aluminum; cesium; palladium; carbon; magnesium; silicon; titanium; chromium; manganese; iron; cobalt; zinc; gallium; germanium; selenium; krypton; rubidium; strontium; zirconium; cadmium; tin; xenon; barium; tantalum; tungsten; iridium; thallium; lead; bismuth; polonium; radium; thorium; uranium; plutonium; americium; californium; einsteinium; fermium; nobelium; rutherfordium; bohrium; teflon; an oxide, an inorganic compound, or a mixture, an alloy or a combination of any of the foregoing.

The nano-particles of the invention may optionally have linker molecules coated or otherwise attached to their surface to enhance or add specific properties. The optional linkers can impart characteristics such as specificities for certain moieties (e.g. bio-molecules, catalysts, analytes, etc.). Additionally, specific moieties or functional groups can also be attached to or associated with the nano-particles herein.

As explained more fully below, some possible materials used for the background surface into/onto which the nano-particles are attached herein, include, but are not limited to: glass; chemically treated glass; silicon; mica; graphine; graphite; aldehyde; epoxy; strepavidin; biotin; silane; agarose; dextran; diamond; magnetic tape; at least one polymer, such as polyethylene glycol (PEG) or oligoethylene glycol (OEG); a carbon nano tube; gold; silver; copper; phosphorous; nickel; carbon; magnesium; titanium; iron; zinc; selenium; cadmium; tin; tungsten; lead; teflon; nitrocellulose; lipids; a hydrogel; a plastic; or rubber, etc.

Of course, it will be appreciated that the current invention is not limited by recitation of particular nano-particle and/or background surface compositions, and that, unless otherwise stated, any of a number of other materials can be used in different embodiments of this invention.

It is to be understood that this invention is not limited to particular configurations, which can, of course, vary (e.g., different combinations of nano-particles and background surfaces, nano-particle coatings/linkers, and optional moieties, etc.). It is also to be understood that the terminology used herein is for the purpose of describing particular embodiments only, and is not intended to be limiting. As used in this specification and the appended claims, the singular forms "a," "an," and "the" include plural referents unless the context clearly dictates otherwise. Thus, for example, reference to "a nano-particle" optionally includes a plurality of such nano-particles, and the like. Likewise, reference to "nano-particles" optionally includes only one nano-particle, unless otherwise stated. Unless defined otherwise, all scientific and technical terms are understood to have the same meaning as commonly used in the art to which they pertain. For the purpose of the present invention, additional specific terms are defined throughout.

Throughout this disclosure, various publications, patents and/or published patent applications are referred to by an identifying citation. The disclosures of these publications, patents and/or published patent applications referenced in this application are hereby fully incorporated by reference into the present disclosure. U.S. Pat. No. 6,730,537: Scaffold-Organized Clusters and Electronic Devices Made Using Such Clusters. U.S. Pat. No. 6,720,157: Chips having Elevated Sample Surfaces. U.S. Pat. No. 6,582,969: Microdevices for High-Throughput Screening of Biomolecules. U.S. Pat. No. 6,406,921: Protein Arrays for High-Throughput Screening A) Nano-Particles "Nano-particle" as used herein refers to more than one, and typically three or more, metal, alloy, semiconductor, magnetic, or other inorganic atoms, coupled to one another by metal-type or ionic bonds. Nano-particles are intermediate in size between single atoms and colloidal materials. Nano-particles made in accordance with the present invention are also referred to herein as "clusters". This indicates that the cross sectional diameter of each such nano-particle is on the order of about 0.1 to 50 nanometers.

The nano-particles will approach spherical in most embodiments, while in others they will be alternative shapes formed by a collection of atoms. In all embodiments the cross sectional diameter of a nano-particle is herein defined as:

The average of three cross sections orthogonal to each other and each passing through the nano-particles center of mass. Furthermore, in some embodiments of the invention, the cross sectional diameter is not as relevant as the "functional" or "exposed" diameter. The functional or exposed area of a nano-particle is that area which is available for interaction with a moiety or linker molecule of interest, i.e. above or level to the immediate surface into or onto which it is attached. The functional or exposed diameter is therefore defined herein as: The diameter of the cross section of a nano-particle whereby the cross section is taken at, and parallel to the boundary of (a) the layer onto or into which the nano-particle is attached, and (b) the surface environment (refer to FIGS. 2(a) and 3).

In some embodiments, the nano-particles attached to the substrate are 'size specific'. In various embodiments this means that the sizes (herein defined as 'average cross-sectional diameters') of size specific nano-particles on a surface show a variance of less than about 1%, or less than about 2%, or less than about 3%, or less than about 4%, or less than about 5%, or less than about 6%, or less than about 7%, or less than about 8%, or less than about 9%, or less than about 10%, or less than about 12%, or less than about 14%, or less than about 16%, or less than about 18%, or less than about 20%, or less than about 25%, or less than about 30%, or less than about 40%, or less than about 50%.

In yet other embodiments, the nano-particles of the invention are not size specific, but, instead, vary in diameter from particle to particle. For example, a wide range of diameters could be desirable due to cost considerations and/or to create a more random surface.

It will be appreciated that the term nano-particles, can include such structures/entities as, e.g., clusters, nano-dots, nano-structures etc. However, the term does not include such structures/entities as nanowires, nanowhiskers, semi-conducting nanofibers, carbon and/or boron nanotubes or nano-tubules, nanorods, nanotetrapods, nanoposts and the like.

The nano-particles of this invention can be substantially homogeneous in material properties, or in certain embodiments they are heterogeneous (e.g. alloys) and can be fabricated from essentially any convenient material or materials. The nano-particles can comprise "pure" materials, substantially pure materials, doped materials and the like and can include insulators, conductors, and semiconductors. In certain embodiments, the nano-particles of this invention are substantially metallic. Additionally, while some illustrative nano-particles herein are comprised of gold, as explained above, they optionally can be comprised of any of a number of different materials, unless otherwise stated. Examples of which include, but not limited to, gold; silver; platinum; copper; phosphorus; nickel; aluminum; cesium; palladium; carbon; magnesium; silicon; titanium; chromium; manganese; iron; cobalt; zinc; gallium; germanium; selenium; krypton; rubidium; strontium; zirconium; cadmium; tin; xenon; barium; tantalum; tungsten; iridium; thallium; lead; bismuth; polonium; radium; thorium; uranium; plutonium; americium; californium; einsteinium; fermium; nobelium; rutherfordium; bohrium; teflon; an oxide, an inorganic compound, or a mixture, an alloy or a combination of any of the foregoing.

The composition of nano-particles can vary depending upon a number of factors, e.g., specific functionalization (if any) to be associated with or attached to the nano-particle, durability, cost, conditions of use, etc. As will be appreciated by people skilled in the art, the nano-particles of the invention can, thus, be composed of any of a myriad of possible substances (or combinations thereof). Thus, any recitation of specific nano-particle compositions herein should not be taken as necessarily limiting.

B) Construction of Nano-Particles

The nano-particles of the invention can be grown, formed, created, or constructed through a variety of different methods, and examples listed herein should not be taken as necessarily limiting. Thus, nano-particles constructed through means not specifically described herein, but which fall within the parameters as set forth herein are nano-particles of the invention and/or are used with the methods of the invention.

In various embodiments herein, the nano-particles involved are created through a sputtering process (including, but not limited to, magnetron sputtering), whereby a target plate is bombarded such that neutral and charged atoms of the target material are released into a chamber. In other words, a material of interest is vaporized to form an energetic cloud of atoms in a plasma. Subsequently, the target atoms condense and combine to form 'clusters' of atoms, the size of which can be controlled through varying the conditions within the chamber and the length of time allowed for cluster formation. The clusters/nano-particles of various sizes can then be accelerated out of the first chamber through a pressure differential and/or ion optics, and the ionized clusters can be focused into a beam using ion-optics. This ionized beam can then be optionally passed through a mass selection stage, whereby the clusters are selected/filtered for size. This mass selection stage can optionally comprise a novel time of flight mass spectrometer. Thus an ionized beam of size specific clusters/nano-particles (or in certain embodiments an ionized beam of clusters/nano-particles of various dimensions) is formed which can be subsequently deposited onto or into a surface.

In other embodiments, the nano-particles of this invention may be created using common methods such as 'attrition' and 'pyrolysis'. In attrition, macro or micro scale particles are ground in a ball mill, a planetary ball mill, or other size reducing mechanism. The resulting particles are air classified to recover nano-particle. In pyrolysis, an organic precursor (liquid or gas) is forced through an orifice at high pressure and burned. The resulting ash is air classified to recover oxide nano-particle. A thermal plasma can also deliver the energy necessary to cause evaporation of small micron-size particles. The thermal plasma temperatures may be in the order of 10000° K, so that solid powder easily evaporates. Nanoparticles are formed upon cooling while exiting the plasma region.

In other embodiments, the nano-particles can be grown in solution through a variety of mechanisms that will be common to those with skill in the art.

C) Construction of Nano-Particle Particle Surfaces

As explained in greater detail below, the nano-particles of the invention can be grown on, formed on, created on, constructed on, attached to, pinned on, embedded into, the surface/substrate through any of a number of different methods and the examples listed herein should not be taken as necessarily limiting. Examples include, but are not limited to, ion beam deposition, magnetron sputtering and subsequent deposition, various chemical growth methods, various evaporation methods, various sputtering methods, various mass selection and subsequent deposition methods etc.

In some embodiments, the nano-particles of the current invention may be deposited onto their ultimate surfaces/substrates with a controlled energy such that they remain stable on the surface/substrate under numerous conditions. The substrate need not be planar and, in fact, can comprise a myriad of three-dimensional conformations. In some embodiments herein, the substrates are flexible.

In various embodiments herein, the nano-particles involved are created through a process of sputtering (including, but not limited to, magnetron sputtering), whereby a target plate is bombarded by gas such that neutral and charged atoms of the target material are released into a chamber. Within the chamber, the target atoms combine to form 'clusters' of atoms, the size of which can be controlled through varying the conditions within the chamber and the length of time allowed for cluster formation. The clusters of various sizes are then accelerated out of the first chamber through a pressure differential, and the ionized clusters are focused into a beam using a set of ion-optics. This ionized beam can then be optionally passed through a mass selection stage, whereby the clusters are selected/filtered for size. Thus an ionized beam of size specific clusters/nano-particles (or in certain embodiments an ionized beam of clusters/nano-particles of various dimensions) is formed. A nano-particle pattered surface may thus be optionally constructed by directing the ionized beam of size selected (or not size selected) nano-particles at a surface onto/into which the clusters/nano-particles can be attached, e.g. pinned or embedded into the surface such that they are stable, i.e. do not move, yet are still protruding from said surface and available to interact with subsequent moieties. In some embodiments, the ionized beam of nano-particles may not be size specific. The depth the nano-particles 'implant' themselves into/onto the surface can be optionally controlled by controlling the energy of the ionized beam in the direction of the surface. The number, density and spacing of the nano-particles can be optionally controlled by controlling the distribution of nano-particles in the ion-beam (for example, through the use of ion-optics), and/or by controlling the concentration of nano-particles present in any unit volume of the ion-beam, and/or controlling the length of time the ion beam is positioned over a unit area on the surface.

In other embodiments, the nano-particles can be grown, formed, created, constructed, through any of a number of different methods common to those with skill in the art (e.g., grown in solution through a variety of mechanisms, and/or created through attrition, and/or pyrolysis etc.), prior to being attached to a surface (to make a nano-particle patterned surface) through a variety of alternate methods. Such alternate methods include, but are not limited to: Passing the grown, formed, created, constructed nano-particles through an electro-spray device to form an ionized beam of nano-particles, which can subsequently be deposited onto/into any given surface by directing the beam at the surface (the beam may be optionally stationary and the surface moving, or the beam moving (e.g. rastering across the surface) and the surface stationary, or the beam and surface stationary, or the beam and surface moving). The depth the nano-particles 'implant' themselves into/onto the surface can be optionally controlled by controlling the energy of the ionized beam in the direction of the surface. The number, density and spacing of the nano-particles can be optionally controlled by controlling the distribution of nano-particles in the ion-beam (for example, through the use of ion-optics), and/or by controlling the concentration of nano-particles present in any unit volume of the ion-beam, and/or controlling the length of time the ion beam is positioned over a unit area on the surface.

In yet other embodiments herein, the nano-particles can be grown on the surface to be used as the substrate, or grown on an alternate surface and transferred to the final surface. A variety of methods may be employed in transferring nano-particles from a surface upon which they are fabricated to another surface. For example, nano-particles may be harvested into a liquid suspension, e.g., ethanol, which is then coated onto another surface. Additionally, nano-particles from a first surface (e.g., ones grown on the first surface or which have been transferred to the first surface) can optionally be "harvested" by applying a sticky coating or material to the nano-particles and then peeling such coating/material away from the first surface. The sticky coating/material is then optionally placed against a second surface to deposit the nano-particles. Examples of sticky coatings/materials which are optionally used for such transfer include, but are not limited to, e.g., tape (e.g., 3M Scotch.®. tape), magnetic strips, curing adhesives (e.g., epoxies, rubber cement, etc.), etc. The nano-particles could be removed from the growth substrate, mixed into a plastic, and then surface of such plastic could be ablated or etched away to expose the particles.

In yet other embodiments, the nano-particles may be transferred or grown onto the surface to form a monolayer. Said monolayer may optionally be covered in a second layer, which may subsequently be etched away to reveal the nano-particle in whole or in part. In such embodiments, the cross sectional diameter of the nano-particles may exceed 50 nm, however the functional or exposed diameter may be less than 50 nm.

There are numerous alternative methods to construct the nano-particles and nano-particle patterned surfaces of the invention, and these alternative methods may be optionally used, and examples listed herein should not be taken as necessarily limiting. Thus, nano-particles and nano-particle patterned surfaces constructed through means not specifically described herein, but which fall within the parameters as set forth herein are still nano-particles and nano-particle patterned surfaces of the invention and/or are used with the methods of the invention.

C) Nano-Particle Characteristics

The nano-particles of this invention can exhibit characteristics of the raw materials/alloys from which they are made (e.g., including, but not limited to, gold; silver; platinum; copper; phosphorus; nickel; aluminum; cesium; palladium; carbon; magnesium; silicon; titanium; chromium; manganese; iron; cobalt; zinc; gallium; germanium; selenium; krypton; rubidium; strontium; zirconium; cadmium; tin; xenon; barium; tantalum; tungsten; iridium; thallium; lead; bismuth; polonium; radium; thorium; uranium; plutonium; americium; californium; einsteinium; fermium; nobelium; rutherfordium; bohrium; teflon; an oxide, an inorganic compound, or a mixture, an alloy or a combination of any of the foregoing). Such characteristics are sometimes also dependent on the size of the associated nano-particles. Alternatively, their characteristics can be altered, modified, and/or enhanced through the properties of small molecule 'linkers' attached to the nano-particles ('linkers' herein means small molecules which can be attached at one end, via chemical or other bonding mechanisms, to one surface, e.g. the nano-particles, such that they can subsequently be attached at their other end, via chemical or other bonding mechanisms, to a moiety of choice, e.g. bio-molecule or catalysts. In other words they link the nano-particle to a moiety via a chosen bonding mechanism). These 'linkers' can be chemically or physically absorbed at one end onto the nano-particles before or after the nano-particles are attached to the first or second surface, with the other functional end free for the subsequent bio-molecule or catalysts attachment. In some embodiments, the chemical linkers have an average length ranging between 0.1 nm and 50 nm, and in particular embodiments between 0.2 nm and 40 nm, or between 0.3 nm and 30 nm, or between 0.4 nm and 20 nm, or between 0.5 nm and 10 nm, or between 0.5 nm and 5 nm, or between 0.5 nm and 1 nm. Examples of such linkers include, but are not limited to, small molecules with carboxyl or amine groups on one functional end, and sulphur groups on the other, e.g. general chemical structures such as, HS—R—COOH, or HS—R—$NH_2$, or (HS—$R_1$)$_n$—$R_2$—COOH, or (HS—$R_1$)$_n$—$R_2$—$NH_2$; where the R, R1, and R2 can be any alkanes, or arenes, or other suitable chemical group. Further, more specific examples include, but are not limited to, 4-mercaptobenzoic acid (HS—$C_6H_4$—COOH), cysteamine (HS—$CH_2$—$CH_2$—$NH_2$), (HS—$(CH_2)_3)_2$—$C_6H_4$—COOH, (HS—$(CH_2)_4$—O)$_2$—$C_6H_4$—$(OCH_2)_{10}$—COOH, and (HS—$(CH_2)_4$—O)$_2$—$C_6H_4$—$(OCH_2)_{20}$—$NH_2$. In some embodiments, the linker molecules could include, but not be limited to, molecules that have one functional end that can be chemically or physically absorbed onto any of the amino acids within a protein (e.g., Alanine, Arginine, Asparagine, Aspartic acid, Cysteine, Glutamic acid, Glutamine, Glycine, Histidine, Isoleucine, Leucine, Lysine, Methionine, Phenylalanine, Proline, Serine, Threonine, Tryptophan, Tyrosine, Valine), and another functional end that can be chemically or physically absorbed direct onto the nano-particles (e.g., gold; silver; platinum; copper; phosphorus; nickel; aluminum; cesium; palladium; carbon; magnesium; silicon; titanium; chromium; manganese; iron; cobalt; zinc; gallium; germanium; selenium; krypton; rubidium; strontium; zirconium; cadmium; tin; xenon; barium; tantalum; tungsten; iridium; thallium; lead; bismuth; polonium; radium; thorium; uranium; plutonium; americium; californium; einsteinium; fermium; nobelium; rutherfordium; bohrium; teflon; an oxide, an inorganic compound, or a mixture, an alloy or a combination of any of the foregoing).

D) Nano-Particle Distribution

The nano-particles of this invention can be distributed over the base surface in a random or ordered format. If the distribution of nano-particles in any one area on the surface is random, the average spacing between the nano-particles may still be optionally controlled. Furthermore, the total number of nano-particles within a unit area of the surface may also be controlled, whether or not the distribution of nano-particles is substantially random, or substantially ordered. Accordingly, the average density of nano-particles within any unit area on a surface may be controlled, whether or not the distribution of nano-particles within that unit area is substantially random, or substantially ordered.

Different regions on the same surface can have different densities, and/or average spacings, and/or numbers of nano-particles attached therein. Each specific region can have a controlled density and/or average spacing, and/or number, of nano-particles attached. Alternatively, each region on the surface, or multiple regions on the surface, or the whole surface, could have a controlled density and/or average spacing, and/or number, of nano-particles attached.

In other embodiments the nano-particles could have a controlled gradient of average spacings, and/or densities, and/or numbers across a surface, such that the density and/or number of nano-particles in any unit area moves from high to low or low to high in a substantially ordered manner.

The number of nano-particles in any unit area on the surface (provided that unit area is at least 200 nano meters squared) may be controlled so as to exhibit a variation of less than about 0.1%, or less than about 0.5%, or less than about 1%, or less than about 2%, or less than about 3%, or less than about 4%, or less than about 5%, or less than about 6%, or less than about 7%, or less than about 8%, or less than about 9%, or less than about 10%, or less than about 12%, or less than about 14%, or less than about 16%, or less than about 18%, or less than about 20%, or less than about 25%, or less than about 30%, or less than about 40%, or less than about 50%, or less than about 100%, or less than 200%. A variation in the number of nano-particles in any unit area on the surface of above 200% is not considered 'controlled'.

The density of nano-particles in any unit area on the surface (provided that unit area is at least 200 nano meters squared) may be controlled to have a variation of less than about 0.1%, or less than about 0.5%, or less than about 1%, or less than about 2%, or less than about 3%, or less than about 4%, or less than about 5%, or less than about 6%, or less than about 7%, or less than about 8%, or less than about 9%, or less than about 10%, or less than about 12%, or less than about 14%, or less than about 16%, or less than about 18%, or less than about 20%, or less than about 25%, or less than about 30%, or less than about 40%, or less than about 50%, or less than about 100%, or less than 200%. A variation in the density of nano-particles in any unit area on the surface of above 200% is not considered 'controlled'.

In other embodiments, each region on the surface, or multiple regions on the surface, or the whole surface, could have a random density and/or average spacing, and/or number, of nano-particles attached.

III) Examples of Nano-Particle Biochip Substrates

In some aspects, the invention comprises a nano-particle biochip substrate that can be used as a substrate for immobilizing and interacting with generic protein content. In some embodiments, the nano-particles of the invention may be functionalized with linkers, or left bare, to facilitate attachment to virtually any protein (e.g. linkers with free carboxyl or amine groups available to bind to the amine or carboxyl groups present at the N and C terminus of proteins). Such embodiments of the nano-particle biochip substrate will not be tailored/optimized for any one type of protein or bio-molecule. Instead, the average spacing, size, material, and functionality of the nano-particles on the surface will be controlled for compatibility with a wide range of protein content.

In some embodiments, the invention comprises a nano-particle biochip substrate that can be used as a substrate for immobilizing and interacting with generic antibody content. In some embodiments, the nano-particles of the invention may be functionalized with linkers to facilitate attachment to any antibody (e.g. linkers with free carboxyl groups available to bind to the amine groups at the base of antibodies). Such embodiments of the nano-particle biochip substrate will be tailored/optimized for generic antibodies, with the average spacing, size, material, and functionality of the nano-particles on the surface controlled for compatibility with a wide range of antibody content.

In other embodiments, the invention comprises a nano-particle biochip substrate that can be used as a substrate for immobilizing and interacting with specific protein (including antibody) content. In some embodiments, the nano-particles of the invention may be functionalized with linkers, or left bare, to facilitate attachment to specific protein (including antibody) groups (including, but not limited to cytokines, or specific mixed sets of proteins linked to disease conditions). Such embodiments of the nano-particle biochip substrate will be tailored/optimized for generic antibodies, with the average spacing, size, material, and functionality of the nano-particles on the surface controlled for compatibility with a wide range of antibody content.

In other embodiments, the invention comprises a nano-particle biochip substrate that can be used as a substrate for immobilizing and interacting with DNA or gene content. In some embodiments, the nano-particles of the invention may be functionalized with linkers, or left bare, to facilitate attachment to DNA or genes.

In other embodiments, the invention comprises a nano-particle biochip substrate that can optionally be used as a substrate for immobilizing and interacting with other bio-molecule content, including but not limited to, proteins or peptides, antibodies or antibody fragments, amino acids; DNA; RNA; genes or portions thereof; lipids; sugars; salts; cell lysates; protein fragments; aptamers; or other biomolecules. In some embodiments, the nano-particles of the invention may be functionalized with linkers, or left bare, to facilitate attachment to these bio-molecules.

In other embodiments, the invention comprises a nano-particle biochip substrate that can be used as a substrate for immobilizing and interacting with catalysts. In some embodiments, the nano-particles of the invention may be functionalized with linkers, or left bare, to facilitate attachment to these catalysts.

In other aspects, the invention comprises a substrate which comprises a microarray comprising one or more regions (each region comprising at least a first surface and a plurality of nano-particles attached to the first or second surface and optionally one or more moiety attached to one or more members of the plurality of nano-particles). In such embodiments, the first region can comprise a different moiety than the second region and the second region different from the third, and so forth, with the result that each separate region comprises different moieties, or some regions comprising the same moiety, or all regions comprising the same moiety. The nano-particles can be attached to the substrate in predetermined patterns, or in a random distribution within the aforementioned regions. The resultant surface can provide an organized array of immobilization regions for one or a plurality of bio-molecule types.

In some embodiments, the bio-molecules will likely be in solution when they contact the chip surfaces. However, there are methods emerging to deposit 'dry' bio-molecules on the chip surface. The invention herein disclosed, (the nano-particle biochip substrate) is not dependent on the method of depositing chosen bio-molecules onto the chip surface.

In other embodiments when bio-molecules are deposited onto the NBS surface, discrete deposits may or may not be left on the surface. For example a liquid containing a bio-molecule of interest may contact the sample surface. The bio-molecule of interest may then bind to the attached nano-particle and substantially all of the liquid medium may or may not be removed from the sample surface. If removed, only the bio-molecule of interest will remain attached to the nano-particle.

In some aspects, an ion-beam may deposit and embed a number of nano-particles comprising respectively size specific nano-particles of inorganic material onto the surface of the chip. A second dispenser may deposit a number of bio-molecules in solution (e.g. a variety of different proteins) on the sample surface. The different bio-molecules (e.g. proteins), sometimes referred to as 'capture agents', will bind to the attached nano-particles. Each bio-molecule (e.g. protein) type will be deposited, and bind, onto nano-particles within a specific region or section on the chips surface (sometimes known as a 'pad'). Accordingly an array of different bio-molecule types will be created on the surface of the chip; with each bio-molecule type gathered in a specific region of the chip. One and only one protein or capture agent may bind directly to an attached nano-particle because of the chosen size and other properties discussed previously of the nano-particle. When the chip has been populated with chosen bio-molecules in any given format, the chip may be referred to as a 'functionalized' biochip chip, and may be used to analyze, produce, or process bio-molecules, samples, and/or analytes of interest (e.g. human serum, drug compounds, organic molecules, inorganic molecules, metals, ceramics, proteins, peptides, polypeptides, nucleic acids, nucleic acid analogs, metallo-proteins, chemical catalysts, metallic groups, antibodies, cells, ions, ligands, substrates, receptors, biotin, hydrophobic moieties, alkyl chains, phenyl groups, adhesive enhancing groups, co-factors, etc. etc.). See FIGS. 7(a) and 7(b).

In some embodiments, the nano-particles used in making the biochip may have selected properties. In some embodiments, the nano-particles may display specific magnetic, electronic (e.g. conductive), optical or other physical properties, which could be used to directly measure and record the occurrence of a bio-molecule binding either directly to the nano-particle, or to another bio-molecule (e.g. a capture agent or agents) already bound to the nano-particle.

In some embodiments, the analysis of the nano-particle biochip substrate may take place using any suitable process and may be quantitative or qualitative. The sample surfaces may be analyzed to determine, for example, which bio-molecules or chemical compounds from a sample of interest bind to the 'functionalized' chip surface (a surface bearing at least one moiety of interest on a nano-particle). In some embodiment, fluorescent tags can be attached to the molecules within the sample of interest, while the proteins bound to the embedded clusters are free of tags and act as capture agents for certain molecules within the sample of interest. In other embodiments once the sample of interest has been incubated with the functionalized NBS, a primary labeled probe molecule can be deposited onto the NBS to facilitate a 'read out' of the interactions on the surface (FIGS. 8(a) and 8(b)). In other embodiments once the sample of interest has been incubated with the functionalized NBS, a primary probe molecule can be deposited onto the NBS without a 'label', followed by a secondary 'labeled' probe molecule deposited on the NBS to facilitate a 'read out' of the interactions on the surface (FIGS. 9(a) and 9(b)).

In some embodiments, binding between the molecules within the sample of interest and the bound proteins can be observed or detected by, any 'labeled' method of detection, including, but not limited to, fluorescence, fluorescence polarization, chemiluminescence, calorimetric detection, luminescence, etc.

In some embodiments, binding between the molecules within the sample of interest and the bound proteins can be observed or detected by, any 'label free' method of detection, including, but not limited to: surface plasmon resonance (SPR), imaging SPR, ellipsometry, or imaging ellipsometry, Fluorescence Resonance Energy Transfer (FRET), magnetic detection methods, electronic detection methods, or any other such method that may result from the unique and specific physical properties of the embedded clusters (FIGS. 10(a) and 10(b), and FIG. 11).

In some aspects, the nano-particle biochip substrate may be made compatible in format to be integrated into any form of biochip system. Such systems may include a variety of surface formats, including but not limited to, a standard 1'×3' micro-array type slide, a 3'×5' 96 well microtiter plate substrate, a 384 well microtiter plate substrate, or a 1,536 well microtiter plate, spherical beads, micro-channel substrate, substrate for mass spectrometry (the mass spectrometry analysis can optionally comprise laser desorption ionization, MALDI, SELDI, or other types of Mass Spectrometry), substrates for lab-on-a-chip systems, substrates for SPR based systems, substrates for colorimetric based systems, substrates designed for ellipsometry based biochip systems, or a substrates designed for Fluorescence Resonance Energy Transfer (FRET) based biochip systems, or chemilluminescent based biochip systems, or a substrate designed for any alternative type of detection method, arraying machine, array scanner, or biochip system. In some embodiments, such substrate(s) can comprise microarray(s) which have a plurality of regions with each region having at least a first surface and a plurality of nano-particles attached to it. Each region can optionally comprise one or more analyte to be assayed (e.g., through one of the aforementioned methods). In other embodiments, substantially each region can comprise a different analyte to be assayed. Such analyte(s) can be optionally attached to or associated with one or more member of the plurality of nano-particles, e.g., the analytes can be optionally immobilized on the substrate surface. Other embodiments comprise wherein substantially each region comprises a different analyte to be assayed. The one or more analyte to be analyzed by the chosen method can optionally be selected from the group consisting of organic molecules, inorganic molecules, metals, ceramics, proteins, peptides, polypeptides, nucleic acids, nucleic acid analogs, metallo-proteins, chemical catalysts, metallic groups, antibodies, cells, ions, ligands, substrates, receptors, biotin, hydrophobic moieties, alkyl chains, phenyl groups, adhesive enhancing groups, co-factors, etc.

In some embodiments, the invention can be integrated into systems for both reverse-phase arrays, capture arrays, and interaction arrays.

In other embodiments, the invention can be integrated into systems for the detection of small molecules like drugs and pesticides for food quality control or diagnostics.

In other embodiments, the invention can be integrated into systems for numerous general biochip applications including, but not limited to: functional proteomic arrays; expression monitoring of proteins during drug profiling and pathway mapping; monitoring of activation-state markers; screening for molecular markers; study of disease progression; quantitative multiplexed analysis of signaling molecules such as kinases, phosphatases or activation-state markers; simultaneous quantitative determination of biomarkers such as cytokines or hormones in serum or enzymes from needle biopsy samples; antibody screening and epitope mapping; general antibody screening; protein profiling; sandwich assays; immunoassays; 2 color direct fluorescence assays; Biomarker discovery; screening protein-protein interactions; screening kinases; identify and validate targets for drug development; peptide arrays, customized peptide arrays; enzyme profiling; mapping protein interactions; domain arrays, phosphotyrosine profiling arrays, cytokine antibody arrays, and angiogenesis antibody arrays; epitope mapping; libraries; protein characterization; angiogenesis arrays; chemokine arrays; inflammatory cytokine arrays; matrix metalloproteinase arrays; phosphorylated kinase arrays; cytokine arrays; isotyping arrays; clone screening selection and optimization; ADME and toxicology; stability testing; QA/QC and batch monitoring; custom-designed proteomics arrays; protein-small molecule interactions; protein-DNA arrays; protein-ligand arrays; quantitation of biomarkers (for various conditions including, but not limited to cancer and heart disease, e.g. cancer and cardiac biomarkers); auto-reactive antibody arrays; tissue extract arrays; etc.

In other embodiments, the invention can be integrated into general diagnostic biochip based systems, whereby one or a set of bio-markers is targeted for detection.

Diagnostic applications include, but are not limited to: the detection and/or quantification of biomarkers for various cancers (including, but not limited to, early and/or later stage ovarian cancer, early and/or later stage lung cancer, early and/or later stage prostate cancer, early and/or later stage skin cancer, early and/or later stage leukemia, early and/or later stage brain tumors, early and/or later stage liver cancer, early and/or later stage colon cancer, etc.); the detection and/or quantification of cardiac biomarkers (for early and/or later stage forms of heart disease), the detection and/or quantification of biomarkers for early and/or later stage HIV; the detection and/or quantification of biomarkers for early and/or later stage dementia; the detection and/or quantification of biomarkers for early and/or later stage depression; the detection and/or quantification of biomarkers for sepsis; the detection and/or quantification of biomarkers for early and/or later stage bladder cancer; etc.

In other embodiments, the invention can be integrated into general bio or chemical sensor based systems, whereby one or a set of bio-molecules or chemical agents is target for detection.

The invention also comprises methods of identifying the presence of at least a first material in a mixture of the first material and at least a second material. Such methods typically comprise providing a substrate having a first and at least a second region, each region comprising at least a first surface and a plurality of nano-particles attached to the first surface and zero, one or more specific moiety (e.g. bio-molecule or catalyst) attached to one or more (at least one) of interest nano-particle. After contacting the mixture with the substrate, the nano-particles and/or the attached moieties interact with the first material, thus, identifying the presence of the material. In some embodiments, the first region comprises a different moiety than that of the at least second region, and the second region comprises a different moiety from the third, etc. In some embodiments, such methods further comprise quantifying the presence of the at least first material based on a level of interaction with the one or more moiety.

The various embodiments of the invention may be used in any number of different fields. For example, embodiments of the invention may be used in pharmaceutical applications such as proteomic (or the like) studies for drug target discovery and/or validation, as well as in diagnostics in a clinical setting for staging or disease progression. Also, embodiments of the invention may be used in environmental analyses for tracking and the identification of contaminants. In academic research environments, embodiments of the invention may be used in biological or medical research. Embodiments of the invention may also be used with research in clinical microarray systems and devices.

In further embodiments of the invention, events such as binding, binding inhibition, reacting, or catalysis between two or more components can be analyzed. For example, the interaction between an analyte in a liquid sample and a capture agent bound to a size specific cluster embedded in a surface may be analyzed using embodiments of the invention: antibody/antigen, antibody/hapten, lectin/carbohydrate, receptor/hormone, protine/RNA, DNA/DNA and the like.

This invention also relates to a method of analyzing a sample (such as a biological sample, such as a body fluid, a tissue, a cell, a cell lysate, water, a food, or a food product) for an analyte of interest, comprising contacting the sample with the nano-particle biochip of the present invention, under conditions under which one or more moiety of interest on the nano-particle biochip binds the analyte of interest, wherein if binding of the analyte of interest to the moiety of interest occurs, the sample contains the analyte of interest. Binding of the analyte of interest to the moiety of interest is determined by use of a fluorescent label or luminescent label, wherein a change in fluorescent signal of the fluorescent label or a change in luminescent signal of the luminescent label in the sample indicates that the analyte of interest is present in the sample. The fluorescent label or the luminescent label is on the moiety of interest; the fluorescent signal or luminescent signal is amplified by the presence of the nano-particle biochip substrate.

The analyte of interest detected can be any of interest, such as an analyte selected from the group consisting of an organic molecule, an inorganic molecule, a metal, a protein, a peptide, a polypeptide, a nucleic acid, a nucleic acid analog, a metalloproteins, an antibody, a cell, an ion, a ligand, a substrate, a receptor, biotin, a hydrophobic moiety, an alkyl chain, a phenyl group, an adhesive enhancing group, a co-factors, and an inorganic molecule the sample is a biological sample. The nano-particles on the biochip can have a cross sectional diameter of from about 0.1 nm. to about 50 nm., from about 1 nm. to about 10 nm. or from about 3 nm. to about 7 nm. The change in fluorescent signal of the fluorescent label or a change in luminescent signal of the luminescent label in the sample can be determined by a variety of approaches, such as by using a fluorescent based biochip reader or luminescent based biochip reader.

This invention also relates to a method of diagnosing or aiding in the diagnosis of a condition in an individual by detecting an analyte of interest in the individual, comprising contacting a sample obtained from the individual with the nano-particle biochip of the present invention, under conditions under which one or more moiety of interest on the nano-particle biochip binds the analyte of interest, wherein the analyte of interest is indicative of the condition and if binding of the analyte of interest to the moiety of interest occurs, the sample contains the analyte of interest, thereby diagnosing or aiding in the diagnosis of the condition in the individual. Binding of the analyte of interest to the moiety of interest can be determined, for example, by use of a fluorescent label or luminescent label, wherein a change in fluorescent signal of the fluorescent label or a change in luminescent signal of the luminescent label in the sample indicates that the analyte of interest is present in the sample. The fluorescent label or the luminescent label can be, for example, on the moiety of interest. In this embodiment, the analyte of interest is selected from the group consisting of an organic molecule, an inorganic molecule, a metal, a protein, a peptide, a polypeptide, a nucleic acid, a nucleic acid analog, a metalloproteins, an antibody, a cell, an ion, a ligand, a substrate, a receptor, biotin, a hydrophobic moiety, an alkyl chain, a phenyl group, an adhesive enhancing group, a co-factors, and an inorganic molecule.

The condition being diagnosed can be any condition for which there is an analyte of interest that is indicative of the condition being diagnosed, such as cancer, coronary heart disease, diabetes, HIV, HIV-AIDS, dementia, depression, sepsis, or a congenital condition.

A further embodiment of this invention is a method of using the nano-particle biochip described herein to assess moiety interactions, wherein: a surface plasmon resonance (SPR) signal is used to detect, analyze or both detect and analyze moiety interactions on the nano-particle biochip, and wherein the nano-particle biochip is read, analyzed or both read and analyzed in an SPR based biochip reader, analysis, or scanner system; an electronic (resistance, capacitance, current) signal is used to detect, analyze or both detect and analyze moiety interactions on the biochip, and wherein the biochip is read, analyzed or read and analyzed, in an electronic (resistance, capacitance, current) based biochip reader, analysis, or scanner system; an optical signal is used to detect, analyze or detect and analyze moiety interactions on the biochip, and wherein the biochip is read, analyzed or read and analyzed, in an ellipsometry based biochip reader, analysis, or scanner system; an optical signal is used to detect, analyze or detect and analyze moiety interactions on the biochip, and wherein the biochip is read, analyzed or read and analyzed, in an Fluorescence Resonance Energy Transfer (FRET) based biochip reader, analysis, or scanner system; an optical signal is used to detect, analyze or detect and analyze moiety interactions on the biochip, and wherein the biochip is read, analyzed or read and/analyzed, in a colorimetric based biochip reader, analysis, or scanner system an optical, magnetic or electronic signal is used to detect, analyze or detect and analyze moiety interactions on the biochip, and wherein the biochip is read, analyzed or read and analyzed, in a bead based biochip reader, analysis, or scanner system; an optical signal is used to detect, analyze or detect and analyze moiety interactions on the biochip, and wherein the biochip is read, analyzed or read and analyzed, in an optical based biochip reader, analysis, or scanner system; or a magnetic signal is used to detect, analyze or detect and analyze moiety interactions on the biochip, and wherein the biochip is read, analyzed or read and analyzed, in a magnetic based biochip reader, analysis, or scanner system.

What is claimed is:

1. A nano-particle biochip substrate, comprising:
a substrate having attached directly thereto, such that each is secured in one position on or in a surface of the substrate and at least some protrude above the surface of the substrate, substantially spherical nano-particles having an average cross sectional diameter of from about 0.1 nm to 50 nm, wherein the nano-particles are distributed in a spatially-controlled manner across the surface and are each useful to directly immobilize only one moiety of interest, and wherein the moiety of interest is selected from the group consisting of a protein or a peptide, an antibody or an antibody fragment, an amino acid, a lipid, a sugar, a salt, a cell lysate, a protein fragment, or a cell.

2. The nano-particle biochip substrate of claim 1, wherein the nano-particles have an average cross sectional diameter of from about 1 nm to about 10 nm.

3. The nano-particle biochip substrate of claim 1, wherein the nano-particles have exposed diameters less than 50 nm.

4. The nano-particle biochip substrate of claim 1, wherein the nano-particles have an average variation in cross sectional diameter of less than 200%.

5. The nano-particle biochip substrate of claim 1, wherein the average distance between a nano-particle and its respective nearest neighboring nano-particles on or in the surface is between about 1 nm and about 200 nm.

6. The nano-particle biochip substrate of claim 5, wherein the average distance between a nano-particle and its respective nearest neighboring nanoparticles on or in the surface in a first region of the surface differs from the average distance between a nano-particle and its respective nearest neighboring nano-particles on or in the surface in a second region of the surface by less than 200%, wherein the first region and the second region each has an area equal to or greater than 100 nm$^2$.

7. The nano-particle biochip substrate of claim 5, wherein the average distance between a nano-particle and its respective nearest neighboring nano-particles on or in the surface varies randomly.

8. The nano-particle biochip substrate of claim 5, wherein the average distance between a nano-particle and its respective nearest neighboring nano-particles on or in the surface varies in a pre-selected pattern across the surface.

9. The nano-particle biochip substrate of claim 1, wherein the number of nano-particles on or in a first region of the surface differs from the number of nano-particles on or in a second region of the surface by less than 200%, wherein the first region and the second region each has an area equal to or greater than 100 nm$^2$.

10. The nano-particle biochip substrate of claim 1, wherein the number of nano-particles on or in a region on the surface varies in a pre-selected pattern relative to the number of nano-particles on or in one or more other regions on the surface, wherein each region has an area equal to or greater than 100 nm$^2$.

11. The nano-particle biochip substrate of claim 1, wherein at least some of the nano-particles have attached thereto at least one respective linker capable of immobilizing the one moiety of interest, and wherein the linker is a small molecule.

12. The nano-particle biochip substrate of claim 11, wherein at least some of the linkers have a specific affinity for at least the one moiety of interest or for at least one specific area or bond on the one moiety of interest.

13. The nano-particle biochip substrate of claim 11, wherein at least some of the linkers are selected from the group consisting of (a) a small molecule with at least one carboxyl group on at least one functional end; (b) a small molecule with at least one amine group on at least one functional end; (c) a small molecule with at least one sulfur group on at least one functional end; and (d) a small molecule with at least one carboxyl group or at least one amine group on one functional end and at least one sulfur group on at least one functional end.

14. The nano-particle biochip substrate of claim 11, wherein at least some of the linkers comprise one functional end able to interact with one or more of the nano-particles on or in the surface of the substrate and a second functional end of the linker is able to interact with an amino acid; a lipid; a sugar; a salt; a cell lysate; a protein; an antibody or antibody fragment; an aptamer; a catalyst; a cell; or a peptide.

15. The nano-particle biochip substrate of claim 11, wherein at least some of the linkers have a formula, prior to being used as a linker, selected from the group consisting of: (a) HS—R—COOH, HS—R—NH$_2$, (HS—R$^1$)$_n$—R$^2$—COOH, (HS—R$^1$)$_n$—R$^2$—NH$_2$; wherein R, R$^1$, and R$^2$ are each independently an alkane or an arene; (b) 4-mercaptobenzoic acid (HS—C$_6$H$_4$—COOH); (c) cysteamine (HS—CH$_2$—CH$_2$—NH$_2$); (d) (HS—(CH$_2$)$_3$)$_2$—C$_6$H$_4$—COOH; (e) (HS—(CH$_2$)$_4$—O)$_2$—C$_6$H$_4$—(OCH$_2$)$_{10}$—COOH; and (f) (HS—(CH$_2$)$_4$—O)$_2$—C$_6$H$_4$—(OCH$_2$)$_{20}$—NH$_2$.

16. The nano-particle biochip substrate of claim 1, wherein:
the average height to which the protruding nano-particles protrude above the surface in a first region of the surface differs from the average height to which the protruding nano-particles protrude above the surface in a second region of the surface by less than 200%.

17. The nano-particle biochip of claim 1, wherein the material of which the surface is composed has an affinity for the one moiety of interest that is less than the affinity of the nano-particles or one or more small molecule linkers attached thereto for the one moiety of interest.

18. The nano-particle biochip of claim 1, wherein the one moiety of interest is attached to at least some of the nano-particles or to one or more small molecule linkers attached thereto.

19. A method of analyzing a sample suspected of containing an analyte of interest, comprising contacting the sample with the nano-particle biochip of claim 18, under conditions in which the one moiety of interest is able to bind the analyte of interest.

20. The method of claim 19, wherein the analyte of interest is selected from the group consisting of an organic molecule, an inorganic molecule, a metal, a protein, a peptide, a polypeptide, a nucleic acid, a nucleic acid analog, a metalloprotein, an antibody, a cell, an ion, a ligand, a substrate, a receptor, biotin, a hydrophobic moiety, an alkyl chain, a phenyl group, an adhesive enhancing group, and a co-factor.

21. The method of claim 19, wherein the sample is a biological sample.

22. The method of claim 21, wherein the biological sample is selected from the group consisting of a tissue, a cell, a cell lysate, a body fluid, water, a food, and a food product.

23. The method of claim 19, wherein binding of the analyte of interest to the one or more moieties of interest is determined using a fluorescent label or a luminescent label.

24. The method of claim 23, wherein the fluorescent label or the luminescent label is attached to the one moiety of interest or to the analyte of interest, or attached to a second moiety which subsequently attaches to the one moiety of interest or to the analyte of interest, and the fluorescent signal or luminescent signal is amplified by at least some of the nano-particles on or in the surface of the substrate.

25. The nano-particle biochip substrate of claim 1, wherein the substrate is selected from the group consisting of: a well, a tube, a channel, a disk, a tape, a sphere, a slide, a microscope slide, a bead, and a chip.

26. The nano-particle biochip substrate of claim 1, wherein at least some of the nano-particles comprise gold; silver; platinum; copper; phosphorus; nickel; aluminum; cesium; palladium; carbon; magnesium; silicon; titanium; chromium; manganese; iron; cobalt; zinc; gallium; germanium; selenium; krypton; rubidium; strontium; zirconium; cadmium; tin; xenon; barium; tantalum; tungsten; iridium; thallium; lead; bismuth; polonium; radium; thorium; uranium; plutonium; americium; californium; einsteinium; fermium; nobelium; rutherfordium; bohrium; teflon; an oxide, an inorganic compound, or an alloy.

27. A method of diagnosing or aiding in the diagnosis of a condition in an individual, the method comprising:
 (a) obtaining a sample from the individual;
 (b) contacting the sample obtained from the individual with the nano-particle biochip of claim 18, under conditions in which the one moiety of interest is able to bind an analyte of interest indicative of the condition to be diagnosed; and
 (c) determining whether binding of the analyte of interest to the one moiety of interest occurs.

28. The method of claims 27, wherein the condition is coronary heart disease, diabetes, HIV, HIV-AIDS, dementia, depression, sepsis, a congenital condition, or cancer.

29. A nano-particle biochip substrate, comprising:
 a substrate having attached directly thereto, such that each is secured in one position on or in a surface of the substrate, nano-particles having an average cross sectional diameter of from about 0.1 nm to 50 nm, wherein the nano-particles are distributed in a spatially-controlled manner across the surface and are useful to directly immobilize only one moiety of interest, wherein the surface of the substrate comprises glass; chemically treated glass; mica; a polymer; polytetrafluoroethylene; nitrocellulose; a hydrogel; a plastic; or rubber.

30. The nano-particle biochip substrate of claim 29, wherein the nano-particles have a cross-sectional diameter of from about 1 nm to about 10 nm.

31. The nano-particle biochip substrate of claim 29, wherein the nano-particles have average exposed diameters less than 50 nm.

32. The nano-particle biochip substrate of claim 29, wherein the surface of the substrate comprises glass.

33. The nano-particle biochip substrate of claim 29, wherein the surface of the substrate consists essentially of glass.

34. A nano-particle biochip substrate, comprising:
 a substrate having attached directly thereto, such that each is secured in one position on or in a surface of the substrate, nano-particles having an average cross sectional diameter of from about 0.1 nm to 50 nm, wherein the nano-particles are useful to directly immobilize only one moiety of interest, and are distributed across the surface such that the number of nano-particles on or in a first region of the surface differs from the number of nano-particles on or in a second region of the surface by less than 1%, wherein the first region and the second region each has an area equal to or greater than 1 $micron_2$, wherein the substrate is produced by a process comprising:
 providing a plurality of nano-particles having an average cross sectional diameter of from about 0.1 nm to about 50 nm; and
 transferring the plurality of nano-particles to the surface of the substrate to produce the substrate having nano-particles attached directly thereto.

35. The nano-particle biochip substrate of claim 34, wherein the nano-particles have a cross-sectional diameter of from about 1 nm to about 10 nm.

36. The nano-particle biochip substrate of claim 34, wherein the nano-particles have an average exposed diameter less than 50 nm.

37. The nano-particle biochip substrate of claim 34, comprising providing the plurality of nano-particles as an ionized beam of particles, and directing the ionized beam of particles to the surface of the substrate to produce the substrate having nano-particles attached directly thereto.

38. A nano-particle biochip substrate, comprising:
 a substrate having attached directly thereto, such that each is secured in one position on or in a surface of the substrate, substantially spherical nano-particles having an average cross sectional diameter of from about 0.1 nm to 50 nm, wherein the nano-particles are distributed in a spatially-controlled manner across the surface and are each useful to directly immobilize only one or more moieties of interest, wherein at least one of the moieties of interest is selected from the group consisting of a protein or a peptide, an antibody or an antibody fragment, an amino acid, a lipid, a sugar, a salt, a cell lysate, a protein fragment, a catalyst or a cell, and wherein at least some of the nano-particles are positioned in one or more cavities in the surface.

39. The nano-particle biochip substrate of claim 38, wherein the nano-particles have a cross sectional diameter of from about 1 nm to about 10 nm.

40. The nano-particle biochip substrate of claim 38, wherein the one or more moieties of interest is a protein or a peptide.

* * * * *